(12) United States Patent  
Linker

(10) Patent No.: US 8,798,727 B2  
(45) Date of Patent: Aug. 5, 2014

(54) LONG-TERM MONITORING FOR DISCRIMINATION OF DIFFERENT HEART RHYTHMS

(71) Applicant: University of Washington, Seattle, WA (US)

(72) Inventor: David Thor Linker, Seattle, WA (US)

(73) Assignee: University of Washington, Seattle, WA (US)

( * ) Notice: Subject to any disclaimer, the term of this patent is extended or adjusted under 35 U.S.C. 154(b) by 11 days.

(21) Appl. No.: 13/670,246

(22) Filed: Nov. 6, 2012

(65) Prior Publication Data

US 2013/0144146 A1     Jun. 6, 2013

Related U.S. Application Data

(63) Continuation of application No. 12/125,859, filed on May 22, 2008, now Pat. No. 8,326,407, which is a continuation-in-part of application No. 11/253,375, filed on Oct. 19, 2005, now Pat. No. 7,630,756.

(60) Provisional application No. 60/620,598, filed on Oct. 19, 2004.

(51) Int. Cl.  
*A61B 5/0452* (2006.01)

(52) U.S. Cl.  
USPC ........... 600/509; 600/515; 600/516; 600/517; 600/518; 600/519

(58) Field of Classification Search  
USPC ......................................... 600/509, 515–519  
See application file for complete search history.

(56) References Cited

U.S. PATENT DOCUMENTS

| | | | |
|---|---|---|---|
| 4,248,244 A * | 2/1981 | Charnitski et al. | 600/519 |
| 5,348,008 A | 9/1994 | Bomn | |
| 6,487,442 B1 | 11/2002 | Wood | |
| 6,701,183 B2 | 3/2004 | Baker | |
| 6,705,998 B2 | 3/2004 | Stergiopoulos | |
| 7,094,207 B1 | 8/2006 | Koh | |

(Continued)

FOREIGN PATENT DOCUMENTS

| EP | 1 219 237 A2 | 7/2002 |
|---|---|---|
| WO | 02/056961 A2 | 7/2002 |
| WO | 03/105020 A2 | 12/2003 |

OTHER PUBLICATIONS

Ang, N.H., "Real-time electrocardiogram signal processing for atrial fibrillation detection," Final report of the postgraduate programme: Mathematics for Industry, Stan Ackermans Institute, Eindhoven University of Technology, Netherlands, 2004, 53 pages.

(Continued)

*Primary Examiner* — Joseph Dietrich  
(74) *Attorney, Agent, or Firm* — Christensen O'Connor Johnson Kindness PLLC

(57) ABSTRACT

A method, system, and device for detection of an arrhythmia, and discrimination between different types of arrhythmia, for example to determine whether to administer an electric shock to the heart, the device comprising a wearable monitor with electrodes that detect the electrical activity of a beating heart, attached to an embedded monitoring system having an amplifier, a microprocessor, a data storage device, and a power supply, all disposed on a substrate having large distal end portions that attach to the electrodes and a narrow intermediate portion that attaches to the monitoring system.

22 Claims, 14 Drawing Sheets

(56) References Cited

U.S. PATENT DOCUMENTS

| | | | |
|---|---|---|---|
| 2002/0052557 | A1 | 5/2002 | Griffin |
| 2002/0147409 | A1 | 10/2002 | Baker |
| 2002/0151806 | A1 | 10/2002 | Starobin |
| 2003/0130586 | A1 | 7/2003 | Starobin |
| 2006/0089559 | A1 | 4/2006 | Barbieri |
| 2006/0167361 | A1 | 7/2006 | Bennett |
| 2007/0179390 | A1 | 8/2007 | Schecter |

OTHER PUBLICATIONS

Bassingthwaighte, J.B., and G.M. Raymond, "Evaluation of the Dispersional Analysis Method for Fractal Time Series," Annals of Biomedical Engineering 23(4):491-505, 1995.

Duverney, D., et al., "High Accuracy of Automatic Detection of Atrial Fibrillation Using Wavelet Transform of Heart Rate Intervals," Pacing and Clinical Electrophysiology 25(4, Part 1):457-462, Apr. 2002.

"Geratherm Awarded Licence for Cardio Monitor," Geratherm Medical AG, May 26, 2004, <http://www.geratherm.com/en/iv_pressemitteilungen>, 4 pages. [retrieved Jan. 26, 2006].

"How It Works," © 2002 CardioNet, <http://www.cardionet/how.html>, 1 page [retrieved Jan. 26, 2006].

Instromedix, A Card Guard Company, © 2004 Card Guard® Group of Companies, <http://www.instromedix.com>, 1 page [retrieved Jan. 26, 2006].

Israel, C.W., et al., "Long-Term Risk of Recurrent Atrial Fibrillation as Documented by an Implantable Monitoring Device: Implications for Optimal Patient Care," Journal of the American College of Cardiology 43(1):47-52, 2004.

Malik, M., "Heart Rate Variability. Standards of Measurement, Physiological Interpretation, and Clinical Use," European Heart Journal 17(3):354-381, Mar. 1996.

Page, R.L., et al., "Asymptomatic or "Silent" Atrial Fibrillation: Frequency in Untreated Patients and Patients Receiving Azimilide," Circulation 107(8):1141-1145, 2003.

Swerdlow, C.D., et al., "Detection of Atrial Fibrillation and Flutter by a Dual Chamber Implantable Cardioverter-Defibrillator," Circulation 101(8):878-885, 2000.

Tateno, K., and L. Glass, "Automatic detection of atrial fibrillation using the coefficient of variation and density histograms of RR and ΔRR intervals," Medical and Biological Engineering and Computing 39(6):664-671, 2001.

Wolk, R., et al., "The incidence of asymptomatic paroxysmal atrial fibrillation in patients treated with propranolol or propafenone," International Journal of Cardiology 54(3):207-211, 1996.

European Search Report mailed Sep. 28, 2009, issued in corresponding European Patent Application No. EP 05809951.6, filed Oct. 19, 2005, 2 pages.

European Examination Report mailed Jan. 13, 2010, issued in corresponding European Patent Application No. EP 05809951.6, filed Oct. 19, 2005, 11 pages.

International Search Report and Written Opinion mailed Jan. 20, 2010, issued in corresponding International Application No. PCT/US2009/044957, filed May 22, 2009, 6 pages.

\* cited by examiner

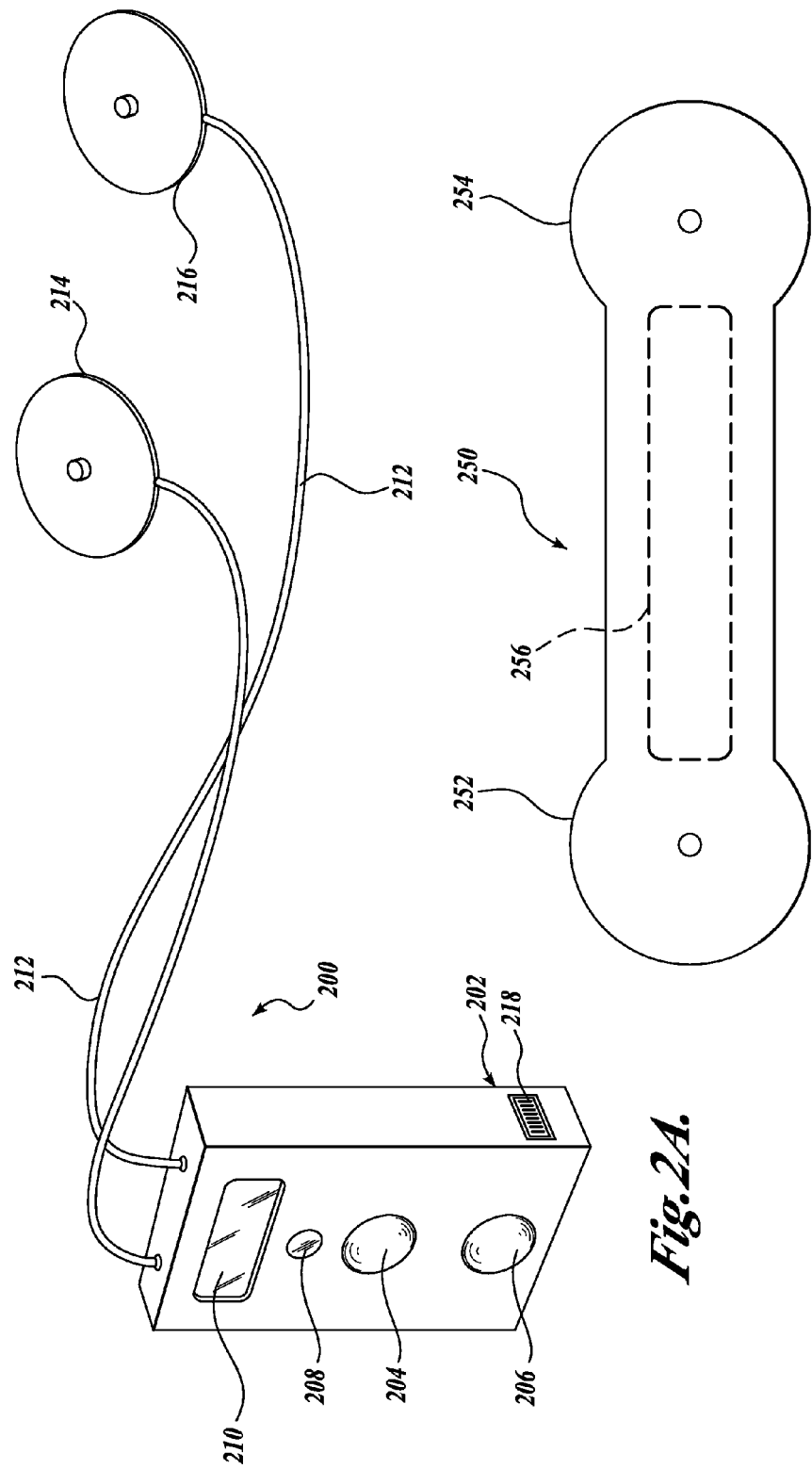

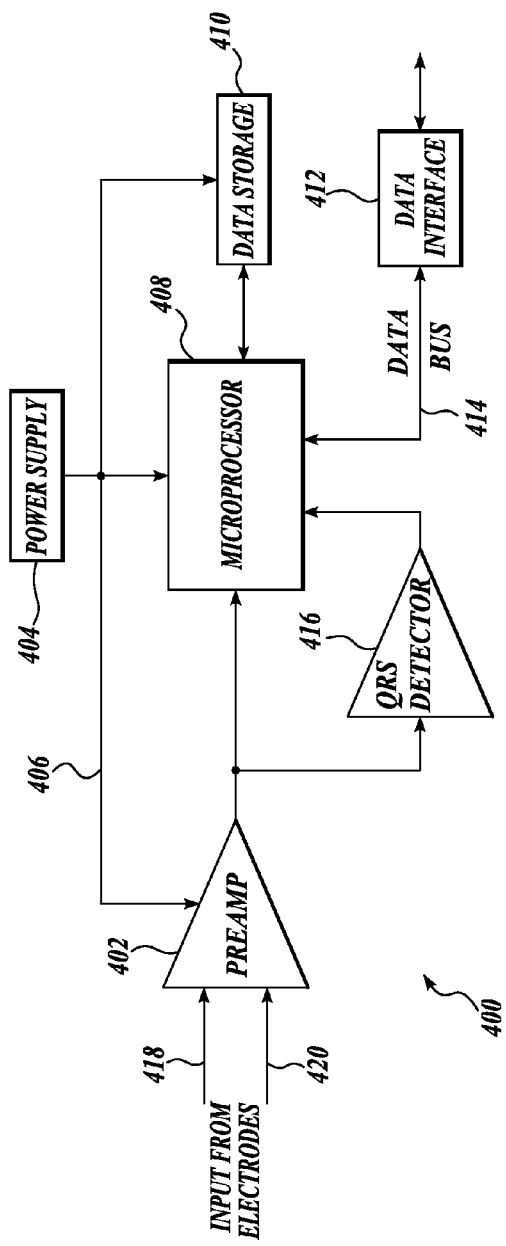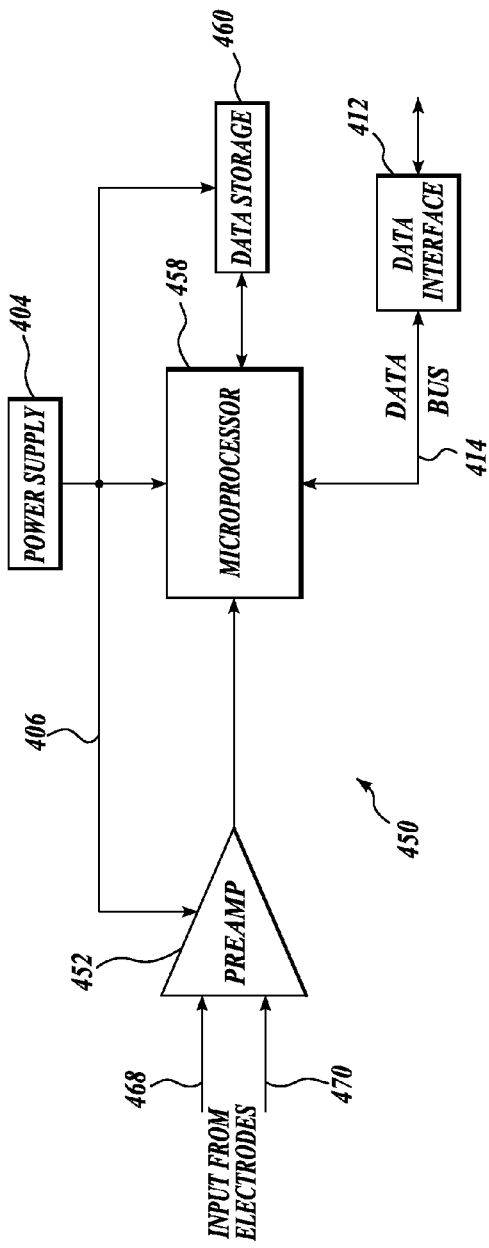

LONG-TERM MONITORING FOR DISCRIMINATION OF DIFFERENT HEART RHYTHMS

CROSS-REFERENCES TO RELATED APPLICATIONS

This application is a continuation of U.S. patent application Ser. No. 12/125,859, filed May 22, 2008, which is a continuation-in-part of U.S. application Ser. No. 11/253,375, filed Oct. 19, 2005 (now U.S. Pat. No. 7,630,756), which claims the benefit of Provisional Application No. 60/620,598, filed Oct. 19, 2004, the entire disclosures of which are hereby incorporated by reference herein.

BACKGROUND

Various groups of heart rhythm disorders are known, some of which are life-threatening and require immediate attention and treatment, such as ventricular fibrillation and ventricular tachycardia, and others which may require treatment but not as immediately, such as atrial fibrillation. Atrial fibrillation ("AF"), for example, is a common rhythm disturbance of the heart associated with increased risk of stroke and death. Ventricular fibrillation is much less common, but it always results in death within minutes, unless it is converted to a less dangerous rhythm. Ventricular tachycardia is also not common, but may result in death if not treated promptly.

Currently, AF is diagnosed by symptoms or is discovered incidentally. Available evidence indicates that a significant portion of patients with AF do not have symptoms, and consequently may not be discovered during routine medical examinations unless they happen to be in atrial fibrillation at the time of the examination. However, AF may be diagnosed using medical equipment, such as rhythm monitors. Monitoring techniques used by available rhythm monitors include monitoring the heart rhythm for a short period of time or intermittently. Unfortunately, these monitoring techniques have low sensitivity for the detection of AF if it is not present during the short monitoring period. Conventional rhythm monitors have limited storage capacity for storing monitoring data used to determine the extent of AF.

AF is the most common disturbance of the heart rhythm requiring treatment. Epidemiologic data estimates that 2.2 million individuals suffer from AF in the United States. The incidence of AF increases with age. The prevalence of AF is approximately 2-3% in patients older than 40 years of age and 6% in those individuals over 65 years and 9% in individuals over 80 years old. Feinberg, W. M., et al., *Prevalence, Age Distribution, and Gender of Patients With Atrial Fibrillation*, 155 Arch. Intern. Med. 469 (1995). As the U.S. population ages, AF will become more prevalent. It is estimated that over 5 million Americans will suffer from AF by the year 2050. Go, A. S., et al., *Prevalence of Diagnosed Atrial Fibrillation in Adults: National Implications for Rhythm Management and Stroke Prevention: the Anticoagulation and Risk Factors in Atrial Fibrillation (ATRIA) Study*, 285 JAMA, 2370 (2001). AF is associated with a doubling of mortality rate of people afflicted with AF compared to people who are not, and an increased risk of stroke of about 5% per year. Fuster, V., et al., *ACC/AHA/ESC Guidelines for the Management of Patients With Atrial Fibrillation*, 22 Eur. Heart J. 1852 (October 2001).

AF can be either symptomatic or asymptomatic, and can be paroxysmal or persistent. Symptomatic AF is a medical condition wherein symptoms are readily detectable by experts in the field. AF is usually diagnosed when a patient reveals associated symptoms or complications, such as congestive heart failure or stroke. AF may also be diagnosed incidentally during a routine medical evaluation. Asymptomatic AF is a medical condition wherein symptoms normally associated with AF are either absent or are not readily detectable by experts in the field.

Paroxysmal AF comprises occasional episodes of the AF condition in the patient. Persistent AF is a continuous existence of the condition. Patients with asymptomatic paroxysmal AF may be exposed to the risk of devastating consequences such as stroke, congestive heart failure, or tachycardia mediated cardiomyopathy, for years before a definitive diagnosis of AF can be made.

Current standard techniques and devices for detecting AF include a resting electrocardiogram, which records about 15 seconds of cardiac activity, a Holter monitor, which records 24-48 hours of cardiac activity during routine daily activities, and an event monitor, which only records cardiac activity when the patient activates the monitor because the patient has detected symptoms associated with AF. These diagnostic methods and tools have significant limitations in diagnosing AF and assessing the efficacy of treatment because of the limited recording time windows of these methods and tools. The prevalence of asymptomatic AF is difficult to assess, but is clearly underrepresented in the figures quoted above.

Pharmacologic treatment of AF may convert patients with symptomatic AF into patients with asymptomatic AF. In a retrospective study of four studies comparing Azimilide drug to placebo where, in the absence of symptoms, routine transtelephonic electrocardiograms were recorded for 30 seconds every two weeks, asymptomatic AF was present in 17% of the patients. Page, R. L., et al., *Asymptomatic or "Silent" Atrial Fibrillation: Frequency in Untreated Patients and Patients Receiving Azimilide*, 107 Circulation 1141 (2003).

In another study of 110 patients with permanently implanted pacemakers who had a history of AF, the condition was diagnosed in 46% of the patients using electrocardiogram ("EKG") recording and in 88% of the patients using stored electrograms recorded by the implanted pacemaker. Israel, C. W., et al., *Long-Term Risk of Recurrent Atrial Fibrillation as Documented by an Implantable Monitoring Device*, 43 J. Am. Coll. Cardiol. 47 (2004).

Review of data stored in implanted devices, such as pacemakers, revealed that 38% of AF recurrences lasting greater than 48 hours were completely asymptomatic. Finally, using data obtained from ambulatory monitors used on patients with paroxysmal AF over a 24-hour period, studies show a high frequency of occurrence of asymptomatic AF among patients treated with propranolol or propafenone drugs. Wolk, R., et al., *The Incidence of Asymptomatic Paroxysmal Atrial Fibrillation in Patients Treated With Propranolol or Propafenone*, 54 Int. J. Cardiol. 207 (1996). In the above-mentioned study, 22% of the patients on propranolol and 27% of the patients on propafenone were diagnosed with AF without symptoms.

There is also evidence that previously undetected AF is associated with stroke. About 4% of patients with stroke admitted to a medical facility also had newly diagnosed AF which was thought to be a precipitating cause of the stroke. Lin, H. J., et al., *Newly Diagnosed Atrial Fibrillation and Acute Stroke, The Framingham Study*, 26 Stroke 1527 (1995).

Under-detection and under-recognition of AF in patients may have significant clinical consequences. A first consequence includes clinical exposure of patients to a significant risk of cardioembolic stroke before detection of the arrhythmia and initiation of appropriate stroke prevention measures.

A second consequence includes difficulty of assessment of the efficacy of rhythm control intervention. Physicians caring for such patients may erroneously conclude that AF is no longer present and inappropriately discontinue anticoagulation treatments which may lead to a devastating cardioembolic stroke. Consequently, once diagnosed with AF, many patients may be committed to life-long anticoagulation by the physician to avoid the latter issues.

A third consequence includes overestimation of successful maintenance of sinus rhythm. Clinical studies evaluating the efficacy of various rhythm control strategies may overestimate the successful maintenance of sinus rhythm as many of these studies report symptomatic AF as an endpoint. An accurate long term monitoring device would enhance the diagnostic yield of capturing asymptomatic paroxysmal atrial fibrillation, potentially allowing the safe withdrawal of anticoagulation treatments in patients treated successfully with anti-arrhythmic agents, identifying the patients at risk who are currently not diagnosed as having AF, and providing a more precise measure of the efficacy of pharmacologic and non-pharmacologic rhythm control strategies.

Detection of AF, automatically or manually, based on statistical data, requires the use of thresholds defined with respect to sensitivity and specificity. The thresholds used define the point beyond which a set of data indicate existence of AF. Sensitivity and specificity are defined as follows. In a dichotomous experiment, a given event, e, falls into one of two sets, such as a set of positive events, P, and a set of negative events, N. The set P includes events p and the set N includes events n.

A detection test may be performed to determine that the given event e belongs to the set P or to the set N in a dichotomous experiment. Sensitivity is a measure of how well the detection test can correctly identify the given event e of the set P as belonging to the set P. Such events e that are correctly identified as belonging to the set P are known as true positives ("TP"). Such events e that are misidentified as belonging to the set N are known as false negatives ("FN").

Sensitivity is defined as the ratio of the number of true positive events detected correctly by the test to the total number of actual positive events p. The total number of actual positive events is equal to the sum of the TP and FN. That is, sensitivity=TP/(TP+FN). A low sensitivity detection test will misidentify more positive events as belonging to the set N than a high sensitivity detection test.

Specificity is the dual of sensitivity and is a measure of how well the detection test can correctly identify the given event e of the set N as belonging to the set N. Such events e that are correctly identified as belonging to the set N are known as true negatives ("TN"). Such events e that are misidentified as belonging to the set P are known as false positives ("FP"). Specificity is defined as the ratio of the number of true negative events detected correctly by the test to the total number of actual negative events n. The total number of actual negative events is equal to the sum of the TN and FP. That is, specificity=TN/(TN+FP). A low specificity detection test will misidentify more negative events as belonging to the set P than a high specificity detection test.

A number of techniques have been used for the automated detection of AF from digitized electrocardiograms. One of the techniques used includes the use of intracardiac recordings obtained from implanted devices showing a sensitivity of close to 100% and a specificity of greater than 99%. Swerdlow, C. D., et al., *Detection of Atrial Fibrillation and Flutter by a Dual-Chamber Implantable Cardioverter-Defibrillator*, 101 Circulation 878 (2000).

A method for analysis of the surface monitor leads using a wavelet transform achieved a sensitivity of 96% and specificity of 93% in recordings from patients with paroxysmal atrial fibrillation. Duverney, D. et al., *High Accuracy of Automatic Detection of Atrial Fibrillation Using Wavelet Transform of Heart Rate Intervals*, 25(4) Pacing and Clinical Electrophysiology 457 (2002). At least one group has proposed using wavelets for implantable/wearable monitoring devices. Ang, N. H., *Real-Time Electrocardiogram (ECG) Signal Processing for Atrial Fibrillation (AF) Detection*, Modeling Seminar—Archive (2003).

A prominent characteristic of AF is heart rate variability. There have been attempts to use the variability of heart interbeat ("RR") intervals directly to identify AF, resulting in a sensitivity of 94% and specificity of 97% using a threshold based on the Kolmogorov-Smirnov test. Tateno, K. and Glass, L., *Automatic Detection of Atrial Fibrillation Using the Coefficient of Variation and Density Histograms of RR and ΔRR Intervals*, 39(6) Med. Biol. Eng. Comput. 664 (2001). The Kolmogorov-Smirnov test (*Chakravart, Laha, and Roy,* 1967) is used to decide if a statistical sample belongs to a population with a specific probability distribution.

Long-term monitoring of cardiac activity is desirable for timely detection of AF, but the storage requirements can be prohibitive. To digitize a single channel EKG at 100 samples per second and 10-bit resolution, which constitute near minimum requirements for a high quality signal, for 90 days of continuous recording requires 927 megabytes of storage. Although providing this amount of storage is possible, it is also costly. Advances in electronics allow the design of portable devices that can pre-process and classify the signals to avoid storage of normal rhythms and save the storage capacity for recording of abnormal rhythms indicating existence of atrial fibrillation.

Selective storage of signals that potentially indicate AF as opposed to normal heart rhythm effectively increases the storage capacity and prolongs the recording period. At least two such devices exist in the market. One such device has been developed by Instromedix (San Diego, Calif.), and is available in two versions. Each version can monitor the heart rhythm for up to 30 days, capturing a total of 10 minutes of potentially abnormal EKG. The device weighs about 4 ounces. The other device is based on satellite telephone technology, and transmits the suspect rhythms to a monitoring facility. For such a device, accurate algorithms are also important, since high sensitivity will result in a high probability of detection, and high specificity will avoid transmission and review of normal rhythms.

Recently, another device was announced with a detection rate of 90% and a monitoring storage capacity equivalent to 60 minutes of recorded data. A device for home use which does "momentary" analysis of the electrocardiogram as the patient grasps handles on the device daily is disclosed in U.S. Pat. No. 6,701,183, issued to Baker et al. on Mar. 2, 2004, entitled Long Term Atrial Fibrillation Monitor.

A device is desired for the long-term monitoring of AF that is inexpensive, non-invasive, highly accurate, and convenient for the patient. These requirements at least indicate that the monitoring device should be light and small. As such, a device is desired with low power requirements and with a significant amount of storage. The storage capacity may possibly be extended by using an algorithm for the elimination of EKG data that indicate very low-probability of AF. This algorithm should be small in size and simple in operation to reduce processing power needs and electrical power requirements.

The existing algorithms based on wavelets appear to be overly complex for this type of application, requiring a significant amount of processing and electrical power as well as storage capacity.

As should be apparent to one skilled in the art, there are situations where the accurate detection of AF would be desirable in an implantable device as well. There are implantable devices that are intended solely for diagnosis of rhythm disturbances, and devices implanted for therapy which have additional diagnostic functions. These devices would also benefit from accurate, low computational complexity detection of AF. It should also be apparent that devices intended to treat AF, either by electric shocks delivered to the heart, or medications administered to control atrial fibrillation, such as propafenone, amiodarone or beta-blockers, or to convert AF, such as ibutilide, would benefit from accurate, low-computational cost complexity detection of AF.

For response to and treatment of ventricular tachycardia and ventricular fibrillation in real-time, often an implantable cardiac defibrillator ("ICD") is surgically implanted in the patient and coupled with the heart to monitor heart rhythm and detect these life-threatening rhythm disturbances. The ICD typically includes logic components implemented in software/firmware and/or hardware for detecting arrhythmia. Once life-threatening arrhythmia is detected, the ICD logic component may, based on a discrimination algorithm, determine that some action, such as administering an electric shock (defibrillation), must be taken to treat the arrhythmia.

However, this determination can be erroneous. In some ICDs such inappropriate shocks can occur in 15% of all patients within a 46-month follow-up. Alter, P., et al., *Complications of Implantable Cardioverter Defibrillator Therapy in 440 Consecutive Patients*, 28(9) Pacing and Clinical Electrophysiology, 926 (2005). Certain sub-populations may have a higher rate of inappropriate shocks, for example, this can occur in as many as 38% of younger patients. Costa, R., et al., *Incidence of Shock and Quality of Life in Young Patients with Implantable Cardioverter-Defibrillator*, 88(3) Arq. Bras. Cardiol. 258 (2007). A common cause of inappropriate shock in these patients is AF, although virtually any supraventricular tachycardia can cause an inappropriate shock.

When not needed, an electric shock causes extreme discomfort and/or pain to the patient and may be potentially dangerous. Accordingly, a more accurate discrimination algorithm is needed to discriminate between cases where an electric shock is needed and cases where an electric shock is not needed. One approach that has been used is based on the heart rate, or beat-to-beat intervals, as in a recent study by Mletzko. Mletzko, R., et al., *Enhanced Specificity of a Dual Chamber ICD Arrhythmia Detection Algorithm by Rate Stability Criteria*, 27(8) Pacing and Clinical Electrophysiology 1113 (2004).

Another approach uses the morphology of the electrocardiographic complexes to help discriminate, with a representative recent method being the use of wavelet-transforms. Klein, G. J., et al., *Improving SVT Discrimination in Single-Chamber ICDs: A New Electrogram Morphology-Based Algorithm*, 17(12) J. Cardiovascular Electrophysiology 1310 (2006). In spite of these methods, inappropriate shocks continue to be a problem in such devices.

An additional constraint is that, since the devices are battery powered and implanted, power consumption is a major consideration. Cebrian, A., et al., *Implantable Cardioverter Defibrillator Algorithms: Status Review in Terms of Computational Cost*, 52(1) Biomed. Tech. (Berl) 25 (2007).

The power consumption is related to the complexity of the algorithm, and the hardware required. The ideal algorithm would not require specialized hardware, and would have a low computational complexity, so that power consumption would be low.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A method and a system for long-term monitoring and detection of an arrhythmia, discrimination between different types of arrhythmia, and delivering an electric shock or other therapy upon detection of an appropriate type of arrhythmia, the method comprising determining a number of heart beat intervals; determining an instantaneous heart rate for each of the heart beat intervals; removing the trend of the instantaneous heart rates; determining the variability of the de-trended instantaneous heart rates compared to a mean of the number of instantaneous heart rates; determining a non-linear value that represents the variability of the instantaneous heart rates; using a linear combination of the mean heart rate and the non-linear value to calculate a result; and using the result to discriminate between different types of arrhythmia by comparing the result with a predetermined threshold.

In one illustrative embodiment, an implantable cardiac device for discriminating between different types of arrhythmia is disclosed, the device including a portable power source; electrodes for collecting heart rhythm data from a patient and delivering an electric pulse to the heart upon detection of an appropriate type of arrhythmia; a monitoring circuit coupled to the power source and the electrode, wherein the monitoring circuit analyzes a segment of the collected heart rhythm data to detect an arrhythmia, discriminate between different types of arrhythmia, and deliver an electric pulse to the heart upon a determination that an appropriate type of arrhythmia has been detected; and a memory coupled to the monitoring circuit for storing the heart rhythm data.

A wearable arrhythmia monitoring and detection device is disclosed that includes an elongate substrate with enlarged ends connected by a narrower intermediate section. The enlarged ends incorporate electrodes, and the narrower intermediate portion includes an integrated monitoring system. The monitoring system includes an amplifier that receives electrocardiography signals from the electrodes, a microprocessor that receives amplified signals from the amplifier, a data storage device that stores at least a portion of the data received from the microprocessor, and a power supply. The wearable arrhythmia monitoring and detection device is configured to detect a cardiac arrhythmia, for example atrial fibrillation.

In an embodiment, only electrocardiography data associated with a detected cardiac arrhythmia is stored on the data storage device, and the data may be compressed prior to such storage.

In an embodiment, the monitoring system is configured to perform one or more of the following functions: (i) determine the duration of heart beat intervals from the electrocardiography data for a selected analysis segment comprising a plurality of heart beat intervals; (ii) calculate an instantaneous heart rate for each of the heart beat intervals in the analysis segment; (iii) calculate a test result using the calculated instantaneous heart rates; (iv) compare the test result with a predetermined threshold to discriminate between different types of cardiac arrhythmia; (v) calculate a mean instantaneous heart rate for the analysis segment; (vi) calculate a deviation from the mean instantaneous heart rate for each heart beat interval in the analysis segment; and (vii) determine a median deviation from the mean instantaneous heart rate in the analysis segment; and use the mean instantaneous heart rate and the median deviation to calculate the test result.

In an embodiment, the monitoring system is configured to calculate a test value as a linear combination of the mean instantaneous heart rate and the median deviation. In an embodiment the monitoring system is configured to use an analysis segment comprising between five and nineteen heart beat intervals.

In an embodiment the integrated monitoring system further includes a wave detection device, such as a QRS detector.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2A is a pictorial diagram of the portable atrial fibrillation monitoring and detection device shown in FIG. 1A;

FIG. 2B is a pictorial diagram of the portable atrial fibrillation monitoring and detection device shown in FIG. 1B;

FIG. 4A is a block diagram of an illustrative embodiment of a circuit for monitoring and detection of atrial fibrillation, including a hardware-based QRS signal detector;

FIG. 4B is a block diagram of another illustrative embodiment of a circuit for monitoring and detection of atrial fibrillation;

DETAILED DESCRIPTION

A system and a method for detecting cardiac fibrillation and/or for discriminating between classes of arrhythmia is disclosed. In one embodiment, a method and apparatus for long-term monitoring and detection of atrial fibrillation is disclosed. In another embodiment, a modified version of the method and a device are disclosed for discriminating heart signal data to detect and accurately identify and correctly distinguish life-threatening cardiac rhythms that require an electric shock (defibrillation) from other rhythms that do not require a shock. While the system and method are ideally suited for detecting atrial fibrillation, or discrimination of life-threatening rhythms from other rhythms, the system and method may also find use in other environments. Furthermore, while the system and method are described in portable configurations and environments, the system and method may also find use in fixed and static environments. Thus, it is to be understood that the present invention should not be construed as limited in application to the illustrative embodiments described herein, and such illustrative embodiments should not be construed as limiting.

Figure 1B:
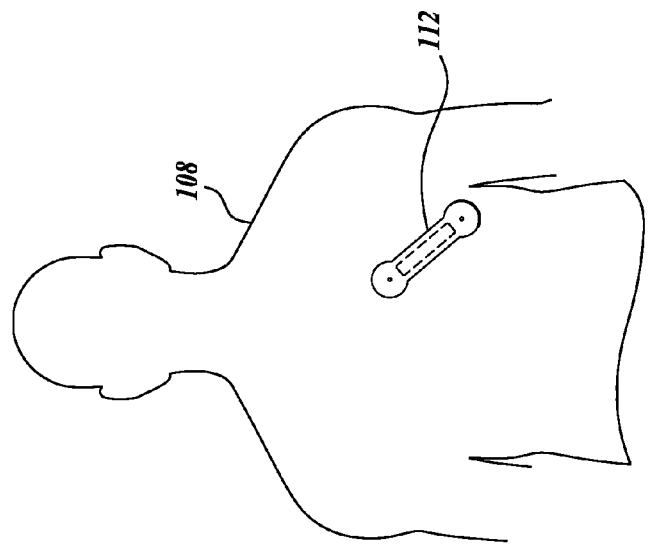
FIG. 1B is a pictorial diagram of another illustrative portable atrial fibrillation monitoring and detection device as applied to a patient.
Figure 1A:
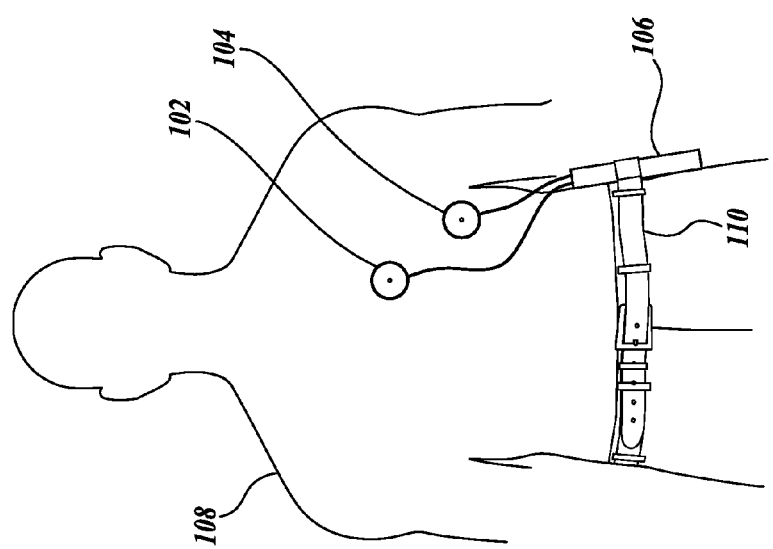
FIG. 1A is a pictorial diagram of an illustrative portable atrial fibrillation monitoring and detection device as applied to a patient.

FIG. 1A is a pictorial diagram showing an illustrative operating environment for a portable atrial fibrillation monitoring and detection device ("portable monitoring device"). This illustrative operating environment includes a light-weight, small, portable monitoring device 106 which can be used by a patient 108 daily or continuously for several months. The portable monitoring device 106 may be carried on a belt 110 or other harness. The portable monitoring device 106 shown includes two electrodes 102 and 104 which are attached to the body of the patient 108 for recording cardiac activity. The electrodes 102 and 104 may be fixed to the portable monitoring device 106 or may be detachably connected to the portable monitoring device 106. The electrodes 102 and 104 may be attached to the body of the patient 108 using various means, including adhesive surfaces, rubber bands, or various kinds of straps and harnesses for holding the electrodes 102 and 104 in place. The electrodes 102 and 104 may also be attached to the body of the patient 108 by being attached to or implanted in the garment of the patient 108. The portable monitoring device 106 continuously collects data related to cardiac activity from the electrodes 102 and 104, and stores some or all of the collected data in the internal storage component of the portable monitoring device 106.

FIG. 1B is a pictorial diagram showing another illustrative operating environment for a portable atrial fibrillation monitoring and detection device wherein the portable monitoring device and attached electrodes are integrated into a unitary monitoring device 112. In this illustrative operating environment, the integrated monitoring device 112 attaches directly to the body of the patient 108 without the need for the belt 110 or other harness for supporting the device. The integrated monitoring device 112 is sufficiently thin and light-weight to securely attach to the body of the patient 108, for example, by means of adhesive surfaces, and to be worn under normal clothes without undue burden. The patient 108 may wear the integrated monitoring device 112 for extended periods of time, removing and re-attaching the integrated monitoring device 112 as necessary for other activities, while noting the times of interruption of the recording operation.

Figure 1C:
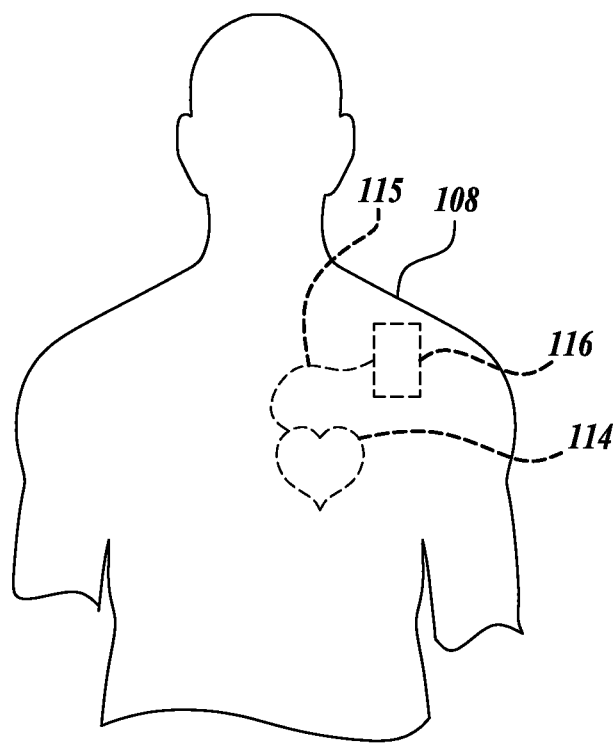
FIG. 1C is a pictorial diagram of an illustrative implantable monitoring and therapeutic device as applied to a patient.

FIG. 1C is a pictorial diagram showing an implantable monitoring, detection, and intervention device 116 implanted into the patient 108. In this example embodiment, the device 116 comprises an implantable cardiac defibrillator 116 that is surgically implanted in the patient 108 and coupled with the heart 114 through one or more leads 115 (one shown). The device 116 monitors heart rhythm to detect arrhythmia, discriminates any detected arrhythmia to identify conditions for which intervention is indicated, and administers the desired intervention. For other arrhythmias not requiring immediate intervention, the device may store the information characterizing the event for transmission or download, either immediately or at a later time.

In certain applications when life-threatening heart arrhythmia is detected (e.g., ventricular fibrillation) therapeutic or remedial action or intervention is needed immediately, such as providing appropriate electrical shock to the heart to stabilize or regulate the heart beat. For example, a patient having a life-threatening heart condition may elect to have an ICD implanted in to continuously monitor heart rhythm and intervene when indicated, for example by providing an appropriate electrical shock to the patient's heart. It is also contemplated that an implantable device 116 may alternatively or additionally be operable to dispense suitable medications in response to a detected arrhythmia.

Figure 1D:
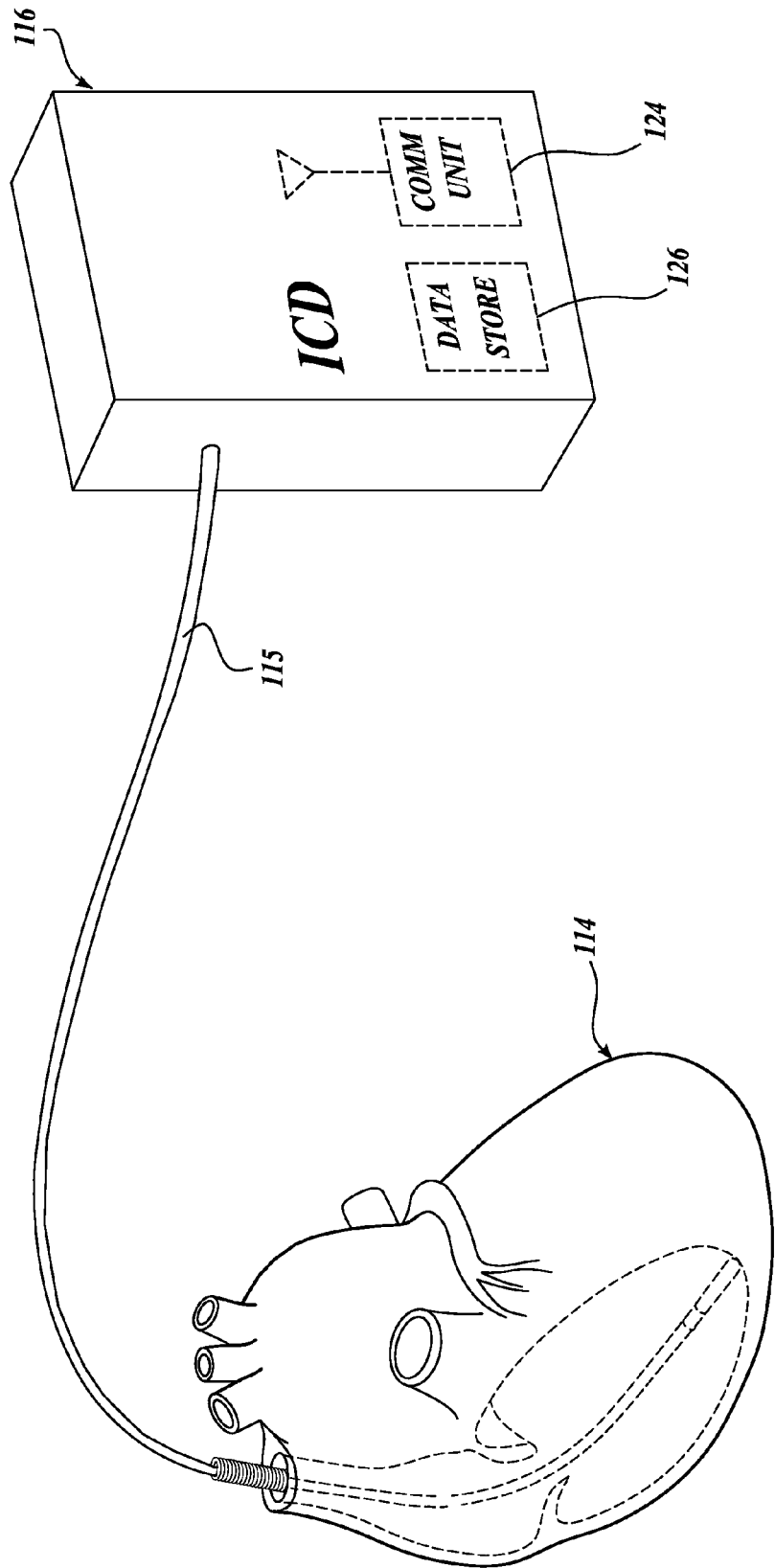
FIG. 1D is a pictorial diagram of the illustrative implantable therapeutic device illustrated in FIG. 1C.

FIG. 1D shows a pictorial diagram of the single-lead ICD 116 shown in FIG. 1C, wherein the right ventricular lead 115 extends into the patient's heart 114. Although a single-lead ICD 116 is shown, it will be apparent that the present invention may be implemented with a multi-lead defibrillator, e.g., a defibrillator having a coronary sinus lead, atrial lead and ventricular lead, as are known in the art. The ICD 116 is surgically implanted in the patient and coupled with the heart 114 to monitor heart rhythm, and to detect and treat arrhythmia when intervention is indicated. In one illustrative embodiment, the ICD 116 includes logic components implemented as embedded software/firmware and/or hardware for detecting arrhythmia, as discussed below. The embedded software may be updateable via wireless communication components 124 incorporated into the ICD 116.

Similarly, data collected and/or generated by the ICD 116 may be stored in a data store 126, which is externally readable from the ICD 116 via the wireless communication components 124, for further analysis. If an arrhythmia is detected, the ICD 116 logic component determines whether a shock must be administered to treat the arrhythmia. The ICD 116 may include other processing components such as a microprocessor/micro-controller for executing software/firmware and controlling other functions of the ICD 116, a power source, such as a battery, and other hardware and/or software components known in the art and commonly used for these types of devices.

With continued reference to FIG. 1D, the ICD 116 is coupled with heart 114 via one or more leads and electrodes 115 to detect arrhythmia and administer electric shock when needed. In this embodiment, the right ventricular lead 115 is used to detect the electrical activity of the heart 114 and to deliver therapeutic electric pulses or shock to the heart 114 in response to the detection of a type of arrhythmia for which electric shock is an appropriate treatment. The determination of the necessity of electric shock and the delivery of such electric shock is performed under the control of the logic components embedded in ICD 116.

An arrhythmia discrimination method is used to determine if a detected arrhythmia is of a type that requires electric shock treatment. If an electric shock is indicated for the type of arrhythmia detected, then the arrhythmia discrimination algorithm will signal the delivery of an electric shock to the heart 114. Otherwise, no electric shock is delivered. The currently preferred discrimination method is described more fully below with respect to FIG. 11B.

FIG. 2A shows an illustrative embodiment of a portable atrial fibrillation monitoring and detection device 202. The device configuration 200 shown includes the portable monitoring device 202, electrodes 214, 216 and leads 212 coupling the electrodes 214, 216 to the portable monitoring device 202. In one illustrative embodiment, the electrodes 214, 216 are fixed to the portable monitoring device 202. In another illustrative embodiment, the electrodes 214, 216 are detachably connected to the portable monitoring device 202. In one illustrative embodiment, the portable monitoring device 202 comprises at least one display 210, such as a liquid crystal display ("LCD") panel, to show various information about the data and the status of the device.

In another illustrative embodiment, the portable monitoring device 202 comprises an indicator 208, such as a light emitting diode ("LED"), to communicate information to the user of the device, for example, by blinking or by using different colors of light. The portable monitoring device 202 further comprises at least one input means 204, such as a button, to control the settings and the behavior of the portable monitoring device 202. In another illustrative embodiment, the portable monitoring device 202 comprises two such input means 204 and 206, one of which may be used by the patient and the other one by a technician during data retrieval or repairs. The portable monitoring device 202 further comprises at least one communication port 218 which is used to download and upload information to and from the portable monitoring device 202, respectively. The information communicated through port 218 includes data collected by the device, device status, device configuration settings, and device software program updates.

In one illustrative embodiment, the portable monitoring device 202 further comprises internal circuitry (not shown in this figure) that include programmable devices, such as a microcontroller or a microprocessor, and internal software programs that are executed by the microcontrollers or microprocessors to cause the portable monitoring device 202 to collect data and perform other functions as discussed below. In another illustrative embodiment, the portable monitoring device 202 comprises internal circuitry (not shown in this figure) that include devices that operate independent of software for some aspects of the operation of the portable monitoring device 202, for example counting wave peaks and wave pattern detection. In one illustrative embodiment, the portable monitoring device has a weight of less than one ounce and a volume of less than ten cubic centimeters. It will be appreciated by those skilled in the art that the shape and dimensions of the portable monitoring device 202 shown in FIG. 2A are for the purpose of illustration and discussion and should not be construed as a limit on the invention.

The portable monitoring device 202 used for detection of arrhythmia and the ICD 116 used for detection, discrimination of different types of arrhythmia, and intervention, may be used as part of one treatment regimen or separately for different medical applications. These devices and the respective algorithms used in each, as more fully described below with respect to FIGS. 11A and 11B, respectively, share certain features and are different in other important ways in terms of design, application, and results they provide.

In one illustrative embodiment the portable monitoring device 202 and the ICD 116 are integrated as functionally distinct units into one integrated implantable device (not shown in the figures) for detection of and discrimination between different types of arrhythmia. In such an integrated device each of the functional detection and discrimination units performs its own function as described below. In such an integrated implantable device, the functional detection and discrimination components may share common functions and features, such as collection of heart rhythm data, computation of mean and median, and other processing tasks and/or hardware/software components that are common to both functional units. In another illustrative embodiment, the portable monitoring device 202 and the ICD 116 are implemented as separate devices that are used in conjunction with each other or separately, as noted above.

FIG. 2B is a pictorial diagram showing another illustrative embodiment of an integrated portable atrial fibrillation monitoring and detection device 250. In this illustrative embodiment, the integrated monitoring device 250 includes a processing component 256 built into the body of integrated monitoring device 250, and at least two integrated electrodes 252 and 254. In another illustrative embodiment, the integrated monitoring device 250 includes more than two integrated electrodes, taking the form of a star with multiple electrode arms extending from the body of the integrated monitoring device 250. In this illustrative embodiment, the integrated monitoring device 250 is sufficiently thin and light-weight to securely attach to the body of the patient, for example, by means of adhesive surfaces, and to be worn under normal clothes without undue burden. In one illustrative embodiment, the integrated monitoring device 250 further comprises internal circuitry (not shown in this figure) that include programmable devices, such as a microcontroller or a microprocessor, and internal software programs that are executed by the microcontrollers or microprocessors to cause the integrated monitoring device 250 to collect data and perform other functions as discussed below. In another illustrative embodiment, the integrated monitoring device 250 comprises internal circuitry (not shown in this figure) that include devices that operate independent of software for some aspects of the operation of the integrated monitoring device 250, for example counting wave peaks and wave pattern detection. It will be appreciated by those skilled in the art that the shape and dimensions of the integrated monitoring device 250 shown in FIG. 2B are for the purpose of illustration and discussion and should not be construed as a limit on the invention.

FIGS. 3A-3D show several illustrative operating environments for downloading and uploading data from/to a portable atrial fibrillation monitoring and detection device. The portable monitoring device 302 shown in the above-mentioned drawings represents all embodiments of such monitoring device, including the portable monitoring device 202 and the integrated monitoring device 250 discussed above.

Figure 3C:
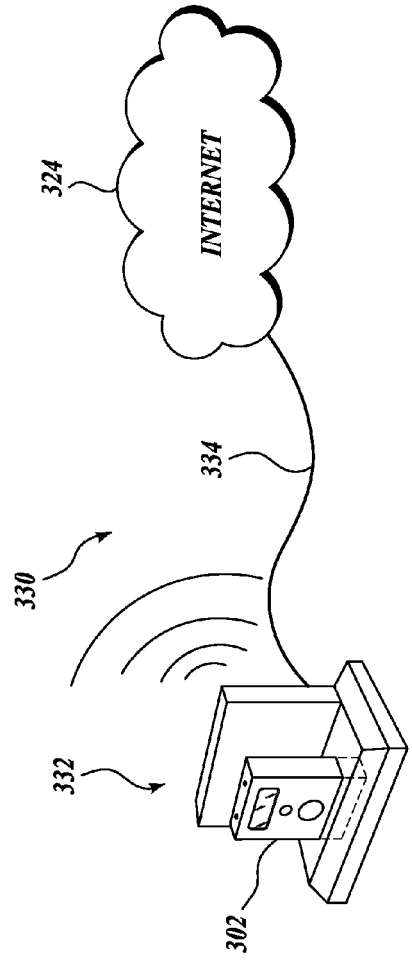
FIG. 3C is a pictorial diagram of another illustrative operating environment for downloading and uploading data from/to a portable atrial fibrillation monitoring and detection device.
Figure 3D:
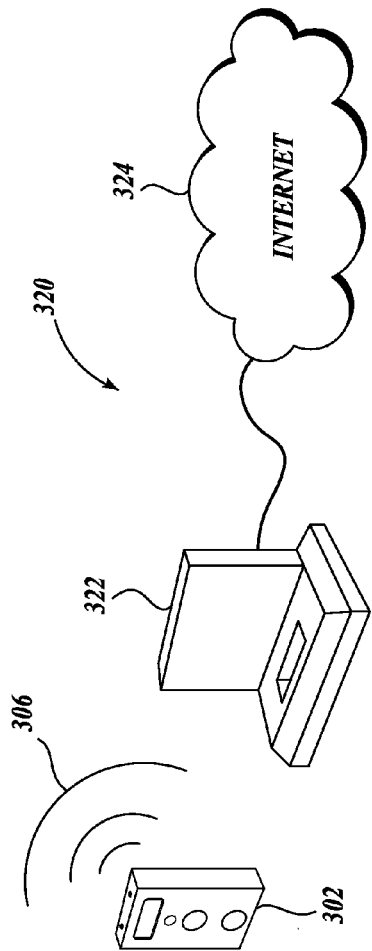
FIG. 3D is a pictorial diagram of another illustrative operating environment for downloading and uploading data from/to a portable atrial fibrillation monitoring and detection device.
Figure 3A:
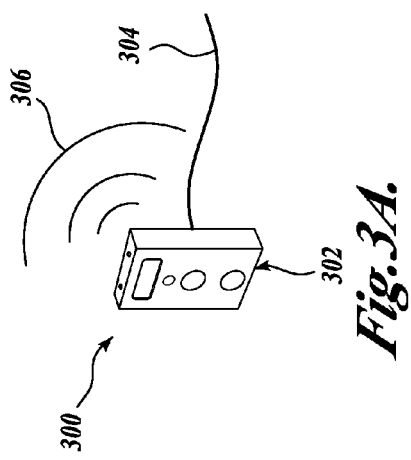
FIG. 3A is a pictorial diagram of an illustrative operating environment for downloading and uploading data from/to a portable atrial fibrillation monitoring and detection device.

FIG. 3A is a pictorial diagram showing an illustrative operating environment 300 for downloading and uploading data from/to a portable atrial fibrillation monitoring and detection device 302. In the operating environment 300, the portable monitoring device 302 communicates with a computer or other data processing equipment at a medical facility or monitoring center (not shown in this figure) where the collected data are used for processing and analysis and maintenance and setup operations are performed on the portable monitoring device 302. In one illustrative embodiment, the portable monitoring device 302 includes a wireless module which communicates data to a computer or other data processing equipment using electromagnetic waves 306. In one illustrative embodiment, the wireless module of the portable monitoring device 302 includes a Bluetooth wireless interface. In another illustrative embodiment, the wireless module of the portable monitoring device 302 includes a ZigBee® wireless interface. As would be clear to one skilled in the art, there are a number of wireless systems or standards that may alternatively be utilized. In another illustrative embodiment, the portable monitoring device 302 uses a wired interface 304, for example, RS232 serial bus, universal serial bus ("USB"), or Firewire, to communicate data. The data communicated by the portable monitoring device 302 includes data collected by the device, device status, device configuration settings, and other similar information. The communication of data may be from or to the portable monitoring device 302. The portable monitoring device 302 may also receive information from outside, for example, from a technician or a computer, using the wireless module or the wired interface 304. Such information may include configuration settings and software program updates.

Figure 3B:
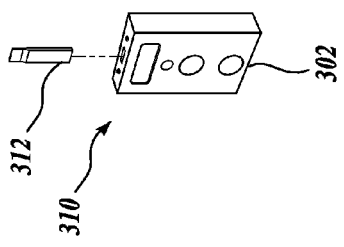
FIG. 3B is a pictorial diagram of another illustrative operating environment for downloading and uploading data from/to a portable atrial fibrillation monitoring and detection device.

FIG. 3B is a pictorial diagram showing another illustrative operating environment 310 for downloading and uploading data from/to a portable atrial fibrillation monitoring and detection device 302. In the operating environment 310, the portable monitoring device 302 communicates with a computer or other data processing equipment at a medical facility or monitoring center (not shown in this figure) where the collected data are used for processing and analysis and maintenance and setup operations are performed on the portable monitoring device 302. In one illustrative embodiment, the portable monitoring device 302 includes a removable memory module 312 which may be removed by a technician at a medical facility or monitoring center for retrieval of data collected by the portable monitoring device 302. In another illustrative embodiment, the memory module 312 is removed by the patient and mailed to the medical facility or monitoring center. Many types of memory devices are available that may be used as embodiments for the memory module 312. For example, in one embodiment, the memory module 312 includes a secure digital ("SD") memory card. In another illustrative embodiment, the memory module 312 includes a Personal Computer Memory Card International Association ("PCMCIA") flash type memory card. Yet in another illustrative embodiment, the memory module 312 includes a compact flash card. Still in another illustrative embodiment, the memory module 312 includes a Multimedia card ("MMC"). Still in another illustrative embodiment, the memory module 312 includes a memory stick. The information contained in the memory module 312 generally includes the data collected by the portable monitoring device 302, but may optionally include other information, such as device status, device configuration settings, and device software program updates. New software program updates for the portable monitoring device 302 may be included in the memory module 312.

FIG. 3C is a pictorial diagram showing another illustrative operating environment 320 for downloading and uploading data from/to a portable atrial fibrillation monitoring and detection device 302. In the operating environment 320, the portable monitoring device 302 communicates with a base station 322 at the patient's home or other remote location away from a medical facility or monitoring center where the collected data is processed and analyzed. The base station 322 may also be used for uploading software program updates, configuration settings, and other information to the portable monitoring device 302. In one illustrative embodiment, the portable monitoring device 302 includes a wireless module which communicates with base station 322 using electromagnetic waves 306. In one illustrative embodiment, the wireless module of the portable monitoring device 302 includes a Bluetooth® wireless interface. In another illustrative embodiment, the wireless module of the portable monitoring device 302 includes a ZigBee® wireless interface. In one illustrative embodiment, the base station 322 is connected to the Internet 324 using various methods of connection, such as a dialup connection, acoustic coupler, wired Ethernet connection, cell phone or wireless Internet connection, such as Wi-Fi®. In another illustrative embodiment, the base station 322 is connected to the medical facility or monitoring center using a direct connection, such as a dedicated network connection, and direct dialup to a server used by the medical facility or monitoring center. The data from the portable monitoring device 302 is transferred to a medical facility or monitoring center where the data is processed and analyzed using the base station 322 and the Internet 324 or other connections, as discussed above.

FIG. 3D is a pictorial diagram showing another illustrative operating environment 330 for downloading and uploading data from/to a portable atrial fibrillation monitoring and detection device 302. In one embodiment, the portable monitoring device 302 is seated in a base station 332 whereby an electrical data interface is used to establish a connection between the portable monitoring device 302 and the base station 332. In one illustrative embodiment, the base station 322 is connected to the Internet 324 using various methods of connection, such as a dialup connection, an acoustic coupler, a wired Ethernet connection, and/or a wireless local area network. In another illustrative embodiment, the base station 322 is connected to the medical facility or monitoring center using a direct connection such as a dedicated network connection and direct dialup to a server used by the medical facility or monitoring center. The data from the portable monitoring device 302 is transferred to a medical facility or monitoring center where the data is processed and analyzed using the base station 332 and the Internet 324 or other connections, as discussed above.

FIG. 4A is a block diagram showing an illustrative embodiment of a circuit 400 for monitoring and detection of atrial fibrillation, including a hardware-based QRS complex signal detector 416 ("QRS detector"). In one illustrative embodiment, the monitoring circuit 400 includes a preamplifier 402 for amplifying the analog electrocardiographic signals detected by electrodes and presented at input terminals 418 and 420. The output of the preamplifier 402 is input to microprocessor 408 and QRS detector 416. In one embodiment, the QRS detector 416 comprises a peak detector. In another embodiment, the QRS detector 416 comprises a peak detector with hysteresis. In yet another embodiment, the QRS detector 416 comprises a signal correlator that matches an input signal to a reference signal (not shown in this figure).

The microprocessor 408 is coupled with a data interface 412 via a data bus 414. The microprocessor 408 is further coupled with a data storage component 410 used for storing data collected by the microprocessor 408 from the preamplifier 402 and for storing software programs executed by the microprocessor 408. A power supply 404 supplies power to all electronic components using power bus 406. In one illustrative embodiment, the power supply 404 comprises a battery. In one illustrative embodiment, the electronic components used in the monitoring circuit 400 are off-the-shelf components. In another illustrative embodiment, the electronic components comprise application-specific integrated circuits or other custom-made electronics. In one embodiment, the microprocessor is a high-integration component including an analog-to-digital converter and memory and data interfaces. The microprocessor and other electronic components are selected to have low power consumption. Low power consumption of electronic components enables the monitoring circuit 400 to operate continuously for extended periods of time on a limited power source, such as a battery. It will be appreciated by those skilled in the art that other electronic components not shown in FIG. 4A, such as LCD display, buttons, LED, and the like, may be coupled to the circuit 400.

The operation of the monitoring circuit 400 includes the pre-amplification of the analog electrocardiographic signals at input terminals 418 and 420 by the preamplifier 402. The amplified analog electrocardiographic signal at the output of preamplifier 402 is transmitted to the microprocessor 408 and QRS detector 416. The microprocessor 408 converts the analog electrocardiographic signal from the output of the preamplifier 402 to a digital electrocardiographic signal suitable for manipulation by a software program running on the microprocessor 408. In one embodiment, the software program running on the microprocessor 408 is stored in a designated section of the data storage component 410. In another embodiment, the software program running on the microprocessor 408 may be stored in a different memory component (not shown in this figure) that is distinct from the data storage component 410. Yet in another embodiment, the software program running on the microprocessor 408 may be stored in a memory component integrated with the microprocessor 408 on the same electronic chip.

The microprocessor 408 receives an output signal of the QRS detector 416 when the QRS detector 416 detects a QRS complex signal which periodically appears as a segment of the electrocardiographic signal. The software program running on the microprocessor 408 analyzes the electrocardiographic signal digitized by the microprocessor 408 and the output signal received from the QRS detector 416 and classifies the digitized electrocardiographic signal as either atrial fibrillation or other cardiac rhythms using an algorithm 1000, described below. The QRS detector 416 reduces the computational load on the microprocessor 408 by detecting the QRS complex signal and notifying the microprocessor 408 by the output signal from the QRS detector 416.

If the digitized electrocardiographic signal is classified as atrial fibrillation, then the digitized electrocardiographic signal is retained as digital electrocardiographic data in the data storage component 410. If the digitized electrocardiographic signal is classified as a cardiac rhythm other than atrial fibrillation, then the digitized electrocardiographic data is not retained in the data storage component 410. Thus, only the digitized electrocardiographic data representing atrial fibrillation is retained in the data storage component 410, saving memory space which would otherwise be used for storing all digitized electrocardiographic data. For example, using a method 1100 (FIG. 11A) for detecting atrial fibrillation, discussed below, and the example given above for 90 days of continuous recording of a single channel EKG at 100 samples per second and 10 bits per resolution, requires about 46 MB of storage rather than 927 MB.

An alternative embodiment would store all data that is recorded, but data classified as atrial fibrillation is marked for earlier review and/or transmission to the medical facility or monitoring center.

In one embodiment, the software program running on the microprocessor 408 compresses the digital electrocardiographic data before storing the digital electrocardiographic data in the data storage component 410. Such compression effectively increases the storage capacity of the data storage component 410. In one embodiment, the monitoring circuit 400 gives an indication to the user of the portable monitoring device 202 (FIG. 2A) that the electrocardiographic data retained in the data storage component 410 is ready for retrieval. In one embodiment, the indication to the user is produced when a predetermined amount of data has been retained in the data storage component 410. In another embodiment, the indication to the user is produced when a predetermined amount of time has elapsed. Those skilled in the art will appreciate that the indication to the user may be produced based on criteria other than those mentioned above. The user of the portable monitoring device 202 retrieves the electrocardiographic data retained in the data storage component 410 by one of the methods discussed above with respect to FIGS. 3A-3D. The electrocardiographic data may be analyzed further by more advanced methods after retrieval.

FIG. 4B is a block diagram showing another illustrative embodiment of a circuit 450 for monitoring and detection of atrial fibrillation. The components and operation of the circuit 450 are substantially similar to the circuit 400 described above with respect to FIG. 4A, except for lacking the QRS detector 416 shown in FIG. 4A. The functions performed by the QRS detector 416 in circuit 400, are performed by a microprocessor 458 under software control. Therefore, the software program stored in a data storage component 460 is executed by the microprocessor 458 to cause the detection of an analog electrocardiographic signal, including a periodic QRS complex segment. The analog electrocardiographic signal is input at input terminals 468 and 470, amplified by a preamplifier 452, and transmitted to the microprocessor 458.

As discussed above with respect to FIG. 4A, the microprocessor 458 digitizes the analog electrocardiographic signal which is used by the software program to detect the periodic QRS complex. The operation of the circuit 450 is otherwise the same as the circuit 400 discussed above. As discussed above, it will be appreciated by those skilled in the art that other electronic components not shown in FIG. 4B, such as LCD display, buttons, LEDs, and the like, may be coupled to the circuit 450.

Figure 5:
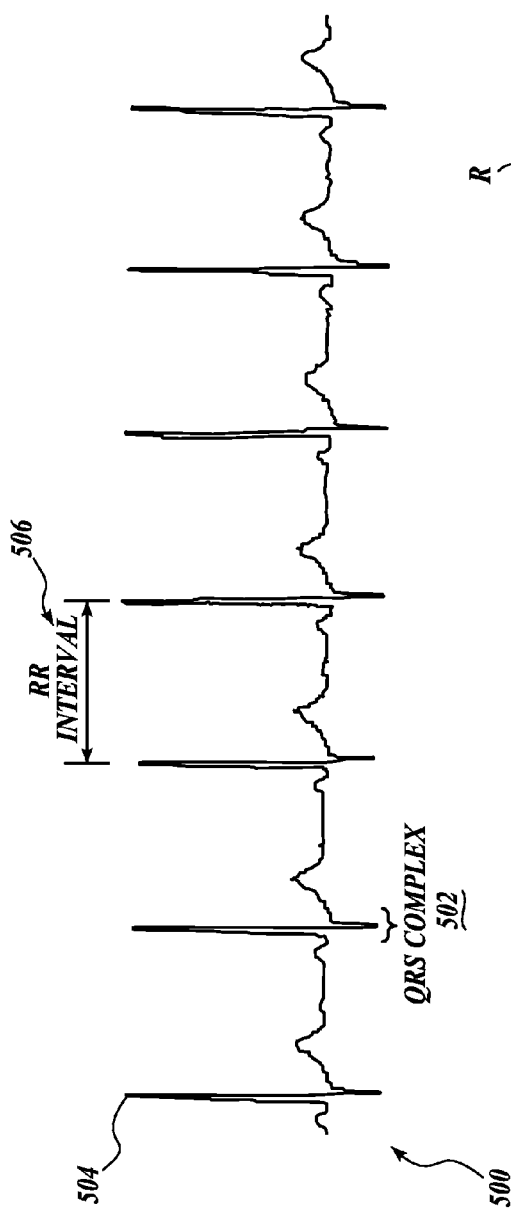
FIG. 5 is a pictorial diagram of a signal representing a heart rhythm.

FIG. 5 shows a signal 500 representing a heart rhythm. The heart rhythm signal 500 comprises a repeating pattern of several distinct segments, including an intermittent event referred to in the art as the QRS complex 502. The QRS complex 502 comprises a peak 504. The time interval between two consecutive peaks 504 is the interbeat interval, or RR interval 506. The peak 504 is one of the QRS complex 502 features which can be used to detect a QRS complex 502. An instantaneous heart rate can be defined as the inverse of the RR interval 506, that is, instantaneous heart rate equals 1/RR-interval (or 60/RR-interval, for beats per minute), for each RR interval 506.

Figure 11A:
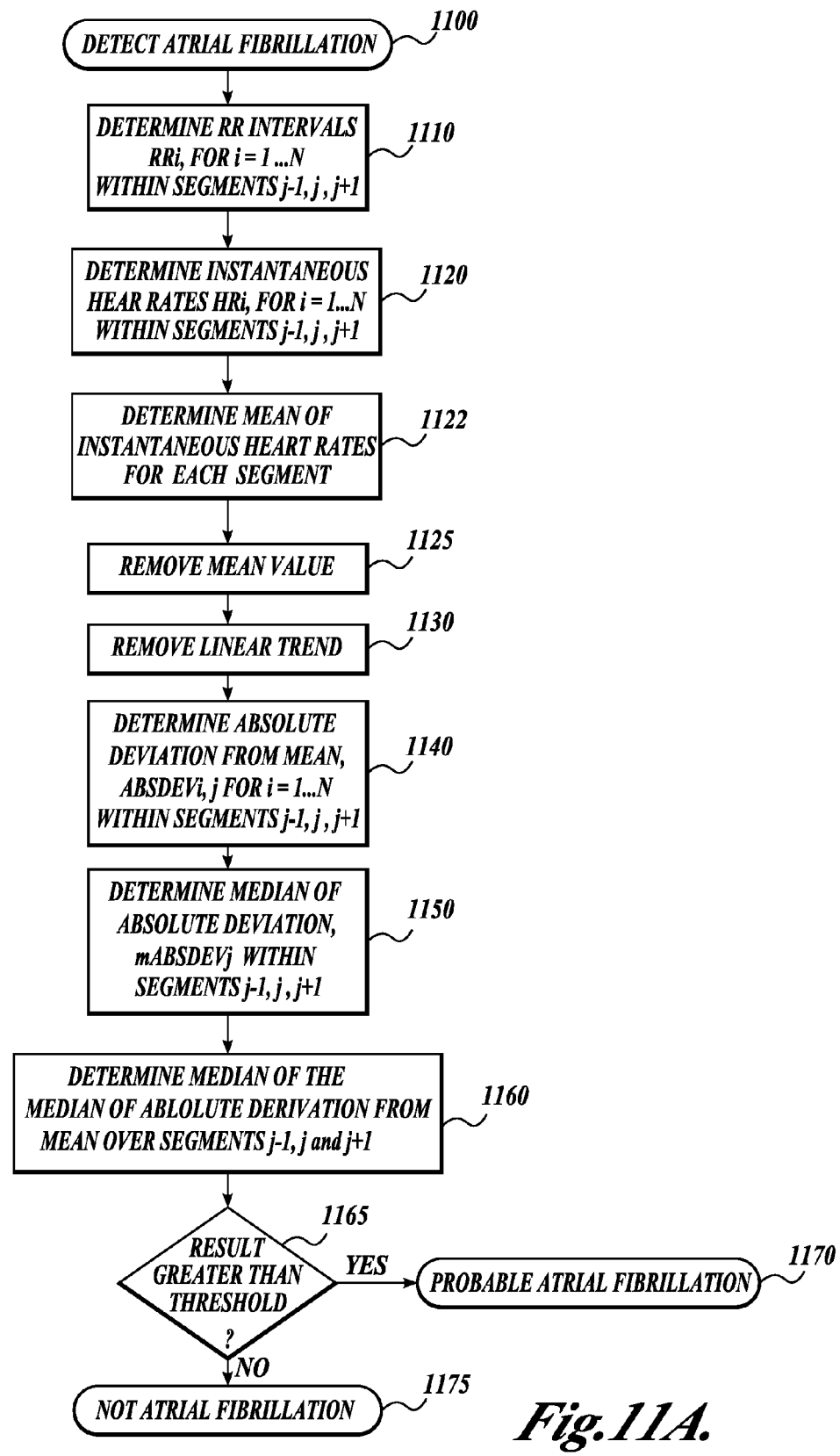
FIG. 11A is a flow diagram of an illustrative atrial fibrillation detection method in accordance with the present invention.

The detection methods 1100 discussed below in more detail with respect to FIG. 11A is used to detect atrial fibrillation by analyzing an electrocardiogram signal 500 with a high degree of accuracy. A discrimination method 1180 discussed below with respect to FIG. 11B shares some of the steps of the detection method 1100, but is directed to discriminating a detected pattern to determine if an arrhythmia is of a type where intervention is indicated. QRS detection methods 1200 are disclosed and discussed with reference to FIG. 12. The disclosed arrhythmia detection and discrimination methods 1100, 1180 are generally based on analyzing the variability of the RR interval 506 to detect and discriminate characteristic of fibrillation. Detection method 1100 uses the actual time of occurrence of the QRS complexes 502 to detect atrial fibrillation.

Figure 6:
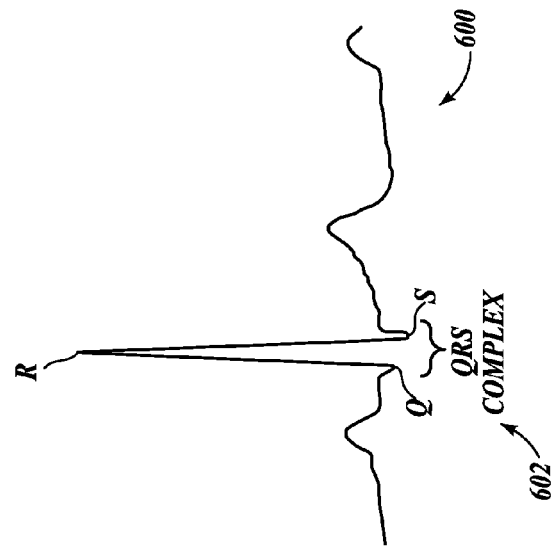
FIG. 6 is a pictorial diagram of a signal representing a QRS portion of the heart rhythm.

FIG. 6 is a pictorial diagram of a heart signal fragment 600 including the QRS complex 602 of a representative heart rhythm. The QRS complex 602 comprises a wave valley section Q, a peak section R, and another valley section S. As discussed above, the QRS complex appears periodically in a heart rhythm. In the present method, the time of appearance of each QRS complex 602 is used to detect the variability of the heart rhythm.

Figure 7:
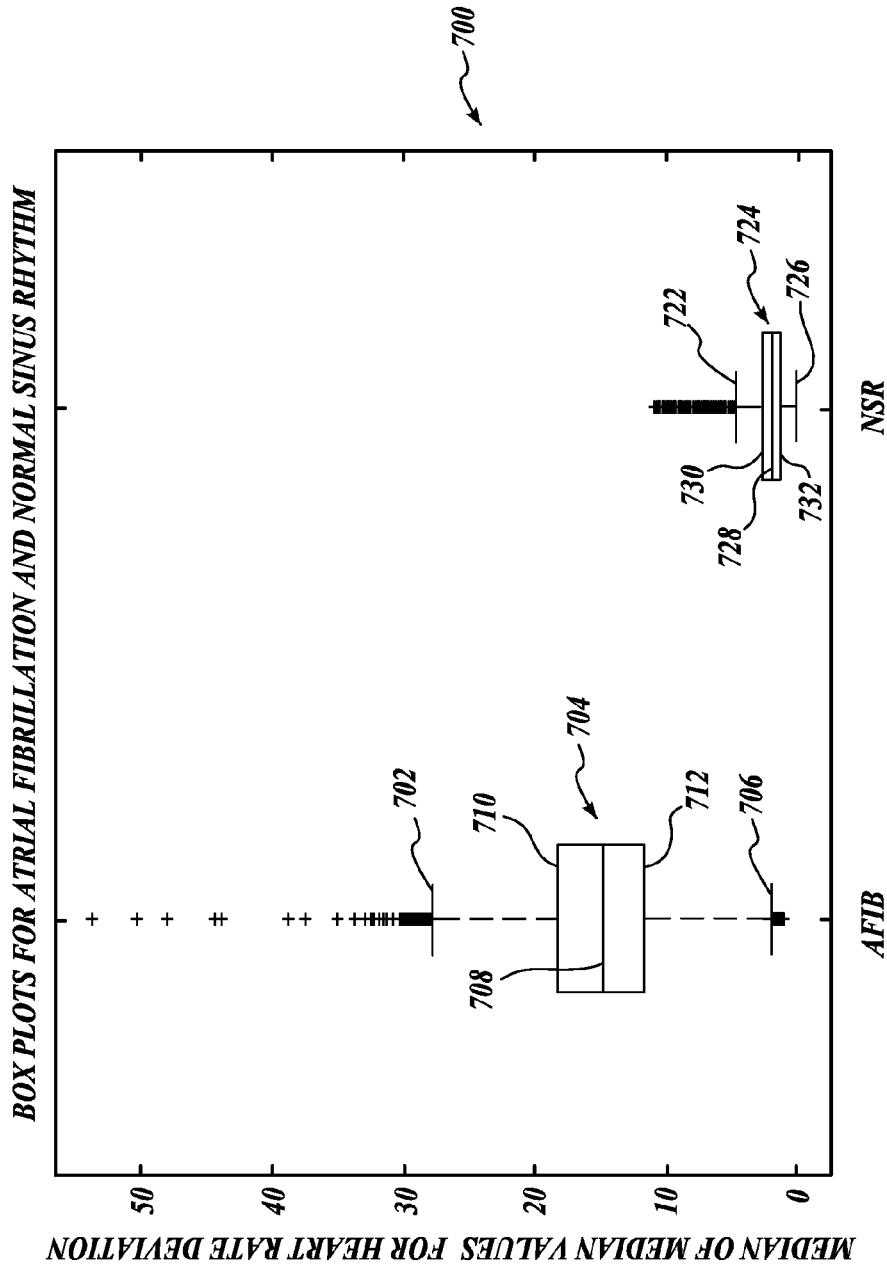
FIG. 7 shows illustrative box plot graphs of values obtained for atrial fibrillation and for a normal heart rhythm.

FIG. 7 is a pictorial diagram comparing illustrative box plots 700 of values obtained for atrial fibrillation 704 and normal heart rhythm 724, using data from the atrial fibrillation and normal sinus rhythm databases of PhysioNet. Goldberger, A. L., et al., *PhysioBank, PhysioToolkit, and PhysioNet: Components of a New Research Resource for Complex Physiologic Signals*, Circulation 101(23):e215-e220 2000 (June 13). The box plots 704 and 724 are constructed based on the calculations described in FIG. 11A, which represent a measure of the local deviation of the heart rate. The local deviation is closely related to variance, indicating the variability of heart rate. Bassingthwaighte, J. B. and Raymond, G. M., *Evaluation of the Dispersional Analysis Method for Fractal Time Series*, 23(4) Ann. Biomed. Eng. 491 (1995). The vertical axis of box plots 700 is the median of median values for heart rate deviation.

The box plot 704 for a typical atrial fibrillation pattern shows a mean value 708, an upper edge 710 indicating the 75th percentile located above the mean 708, a lower edge 712 indicating the 25th percentile located below the mean 708, an upper line 702 indicating 1.5 interquartile (interquartile range is a measure of spread or dispersion and is the difference between the 75th percentile and the 25th percentile) above the mean 708, and a lower line 706 indicating 1.5 interquartile below the mean 708.

In contrast, the box plot 724 for a normal heart rhythm, comprising a mean value 728, an upper edge 730 indicating 75th percentile located above the mean 728, a lower edge 732 indicating 25th percentile located below the mean 708, an upper line 722 indicating 1.5 interquartile above the mean 728, and a lower line 726 indicating 1.5 interquartile below the mean 728, is much more compact.

Based on the variability of heart rate indicated by box plots 704 and 724, significant discrimination between atrial fibrillation and normal sinus rhythm exists, which discrimination is detectable by the method 1100 (FIG. 11A), discussed below, using a median of median values for heart rate deviation. A median of a number of statistical samples is significant because the median is a non-linear average value representing the statistical samples and is defined as the middle value of a sorted list of the statistical samples. It is non-linear with respect to the values of the statistical samples because the value of the median does not change with value of each statistical sample, in contrast to a mean value of the same samples. (The mean value changes linearly with the changes in the values of the statistical samples because the mean is equal to the sum of the values of all the statistical samples divided by the number of the statistical samples.) Thus, the median value is not sensitive to and does not change as a result of changes in sample values at the extreme ends of a statistical population.

Figure 8:
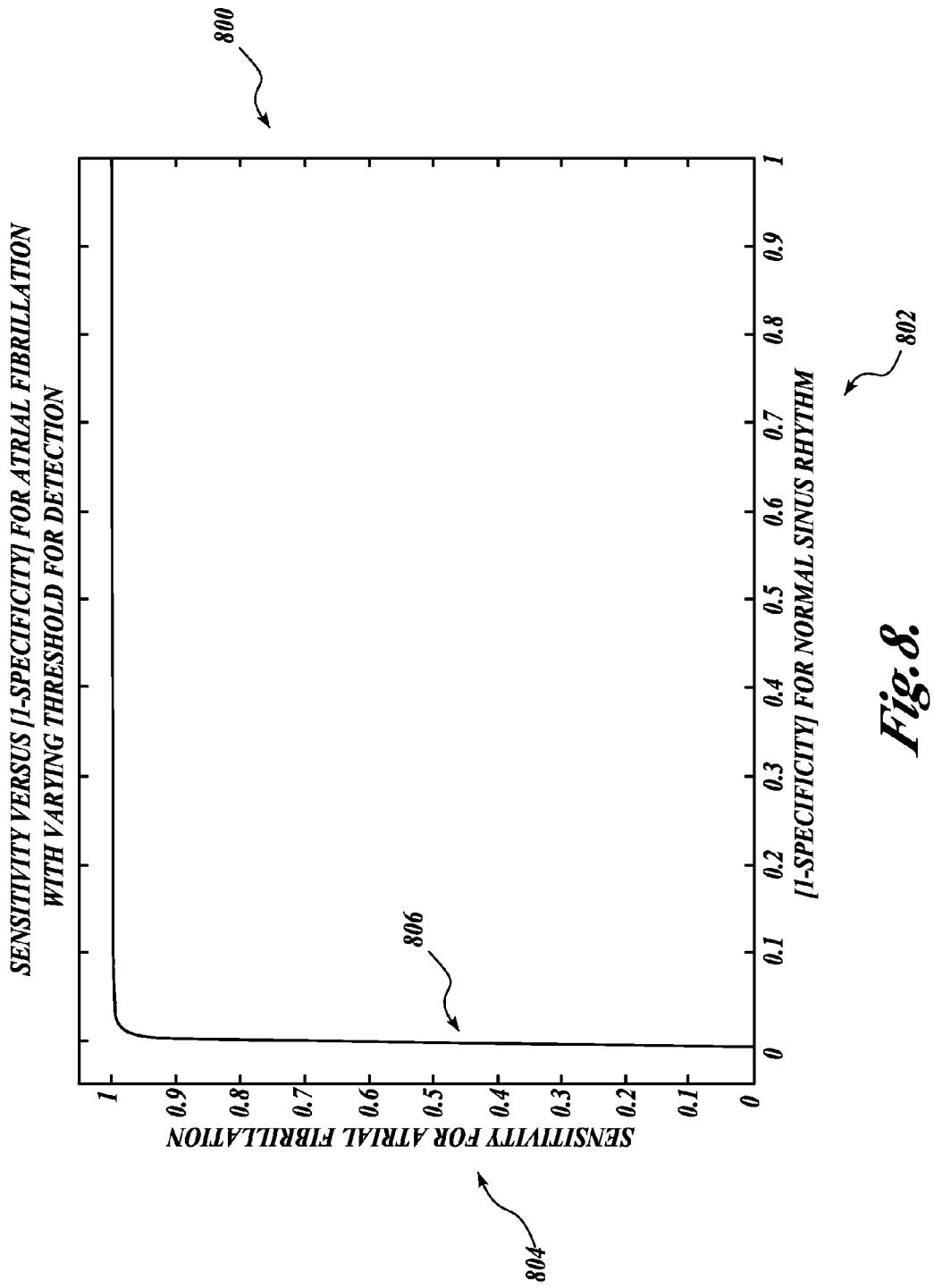
FIG. 8 is an illustrative graph of values for Sensitivity versus (1—Specificity)

FIG. 8 is an illustrative plot 800 of values for sensitivity versus [1—specificity] (one minus specificity) with a variable threshold for detection of atrial fibrillation. The plot 800 comprises a receiver operator curve ("ROC") 806. This ROC 806 relates the sensitivity value 804 versus one minus specificity (1—specificity) value 802, calculated based on different threshold values for the present embodiment comprising a median of median values for heart rate deviation. A median of median values for heart rate deviation, discussed above with respect to FIG. 7, above a given threshold value is considered to indicate atrial fibrillation subject to error rates defined by sensitivity and specificity values. Clearly, if the selected threshold is too low, the low sensitivity for detecting AF will be very good (near or equal to 1.0) but false positives will be high, resulting in poor specificity. Conversely, if the threshold is too high, false positives will be reduced, but actual AF events will be missed (false negatives).

Errors in detection of atrial fibrillation are classified as false positives ("FP") and false negatives ("FN"), as discussed above in the background section. Threshold values are selected such that sensitivity and specificity values are maximized. The bend in the ROC 806 corresponds to a threshold that results in minimal error, that is, maximal sensitivity and specificity.

Figure 9:
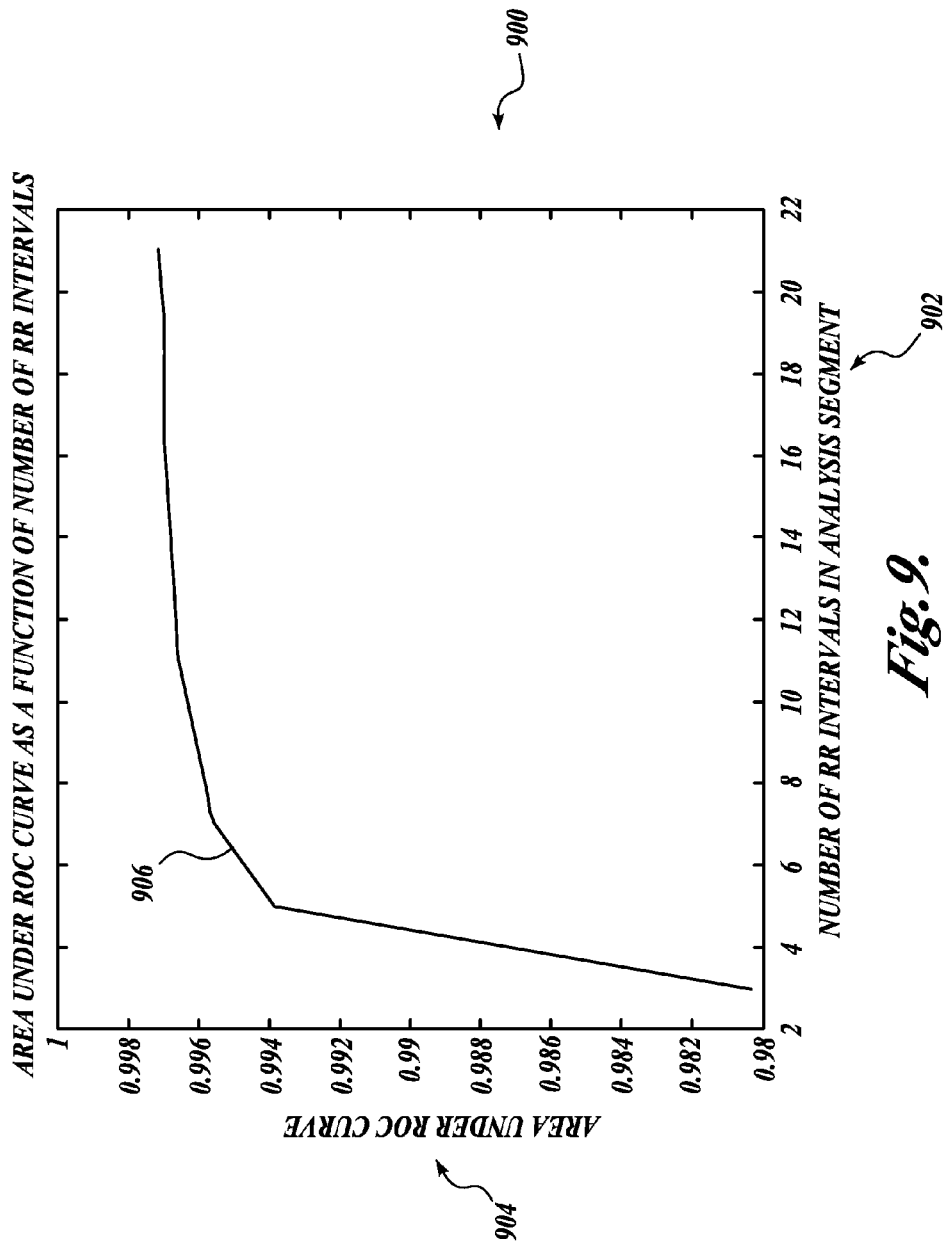
FIG. 9 is an illustrative graph showing a number of RR intervals versus area under a Receiver Operator Curve ("ROC") for the atrial fibrillation detection algorithm.

FIG. 9 is an illustrative plot 900 of a number of RR intervals 902 used to detect AF versus area under the ROC 904. The plot 900 comprises an area under ROC curve 906 obtained by plotting the area under each ROC 806 (e.g., FIG. 8) versus number of RR intervals 902 used in calculating the median of median values for heart rate deviation. Sensitivity and specificity increase when the number of RR intervals 902 increases, resulting in a larger area under the ROC 904, which has a maximum value of 1. The bend in the area under ROC curve 906 corresponds to the number of RR intervals 902 at which the area under ROC curve 906 is near maximum, and increasing the number of RR intervals 902 has less effect to increase the performance of the method, as measured by the area under ROC curve 904 value. Therefore, the use of a larger number of RR intervals 902 only marginally increases the area under ROC curve 906 while increasing the computational load on a portable monitoring device 202. Therefore, by plotting the area under ROC curve 906, a near optimal number of RR intervals 902 may be obtained, minimizing the number of RR intervals 902 to be used in calculations while maximizing the sensitivity and specificity defined by the corresponding ROC 806.

For example, if 19 RR intervals 902 are used for computation, a threshold may be chosen that provides a sensitivity value of 98.0% and specificity value of 98.7%. The above-mentioned sensitivity and specificity values are close to those resulting from using 7 RR intervals 902 (98.0% and 97.2%, respectively), but the cost of computation and storage with 19 RR intervals 902 is greater than with 7 RR intervals 902.

Persons of skill in the art will understand that the desired sensitivity and specificity may vary depending on a number of factors, including for example a particular patient's medical and physical condition, the nature of the particular application, etc. In an application wherein monitoring is conducted in conjunction with an in situ intervention mechanism such as an implantable defibrillator, for example (see FIG. 11B, and the associated disclosure), the importance of intervention in any potentially life-threatening situation may outweigh the risks and discomfort associated with the intervention. Therefore, the threshold may be chosen to achieve a very high sensitivity, with less concern about specificity.

Figure 10:
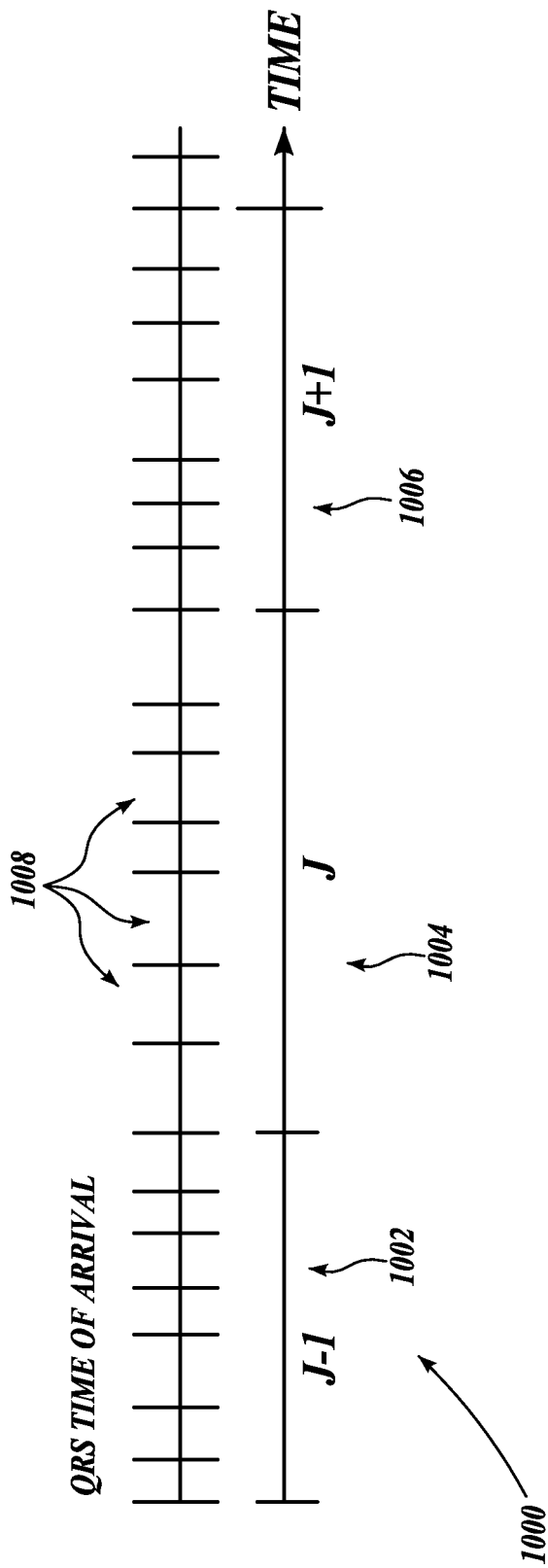
FIG. 10 is an illustrative time line of RR intervals, and showing three segments of seven RR intervals.

FIG. 10 is a pictorial diagram showing an illustrative set of three segments of RR intervals 1008. For the arrhythmia detection algorithm the three segments used include segment J−1 1002, segment J 1004, and segment J+1 1006. Each of the segments J−1 1002, J 1004, and J+1 1006 comprises an equal number of RR intervals 902. Each RR interval is measured based on the arrival time of each QRS complex 502, as shown in FIG. 5. The above-mentioned segments are used in method 1100 discussed below.

For the preferred arrhythmia discrimination method 1180 (see, FIG. 11B) disclosed herein, only a single segment, for example, segment J 1004, is used for computation. As discussed above, the segment J 1004 comprises a predetermined number of RR intervals 1008. Although the illustrative segments shown in FIG. 10 comprise seven heart beat intervals, as discussed above different numbers of heart beat intervals may be selected to comprise an analysis segment. For example, in a preferred embodiment, the analysis segments comprise between three and nineteen heart beat intervals.

FIG. 11A is a flow diagram of an illustrative atrial fibrillation detection method 1100. The method 1100 measures the variability of heart rate using the instantaneous heart rate based on actual arrival times of QRS signals 502. The method 1100 further compares a non-linear value representing the variability of heart rate to a selected threshold. The method 1100 determines the existence of atrial fibrillation based on the result of the comparison. The flow diagram proceeds to block 1110 where the duration of each RR interval 1008 is determined within each of a number of segments, for example, the three segments J−1 1002, J 1004, and J+1 1006 shown in FIG. 10. It will be appreciated by those skilled in the art that any number of segments may be used for this calculation and the choice of three segments is for the purpose of illustration only and is not to be construed as a limitation on the invention. The flow diagram proceeds to block 1120 where instantaneous heart rates corresponding to each RR interval 1108 are determined within each of the segments J−1 1002, J 1004, and J+1 1006 separately.

In block 1122 the mean value of the instantaneous heart rates are calculated for each segment. In block 1125 the mean values of each of the segments J−1 1002, J 1004, and J+1 1006 are subtracted. In block 1130 the linear trend is removed to improve estimation of variability of instantaneous heart rate. In block 1140 the absolute value of the deviation from mean with linear trend removed is determined for each RR interval 1108 within each of the segments J−1 1002, J 1004, and J+1 1006. In block 1150 the median of absolute deviation from mean for each RR interval 1108 is determined. In block 1160 the median of medians of all three segments J−1 1002, J 1004, and J+1 1006 is obtained. In block 1165 the median of medians of all three segments J−1 1002, J 1004, and J+1 1006 is compared with a chosen threshold value. If the median of medians of all three segments J−1 1002, J 1004, and J+1 1006 is greater than the chosen threshold, then existence of atrial fibrillation is probable 1170 in segment J 1004. Otherwise, atrial fibrillation is unlikely to exist 1175 in segment J 1004.

Figure 11B:
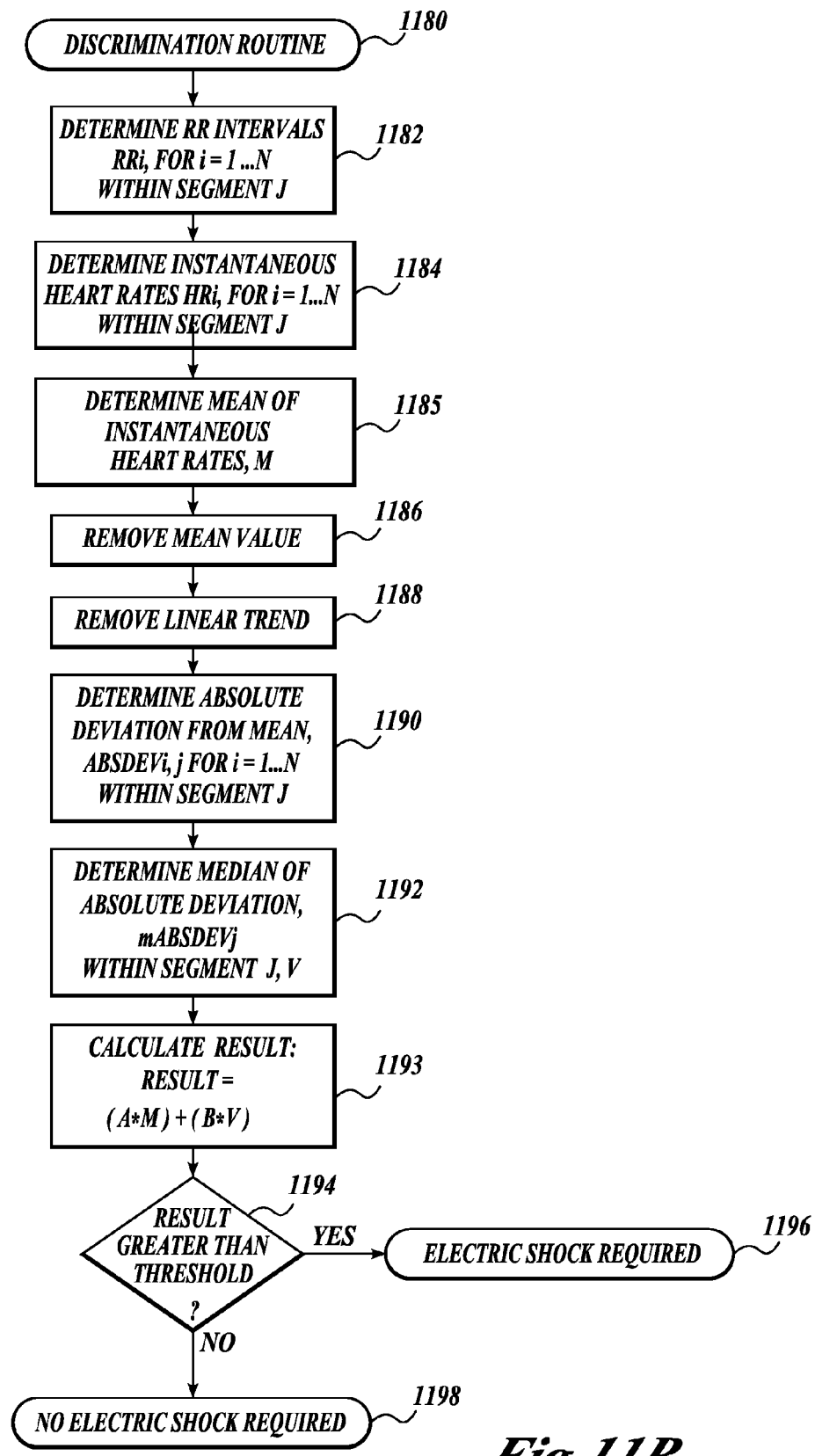
FIG. 11B is a flow diagram of an illustrative arrhythmia discrimination method in accordance with the present invention.

FIG. 11B is a flow diagram of an illustrative life-threatening arrhythmia discrimination method 1180 and is similar to the flow diagram of FIG. 11A in relevant portions. As such, only the differences between the two flow diagrams are described below with respect to FIG. 11B. As noted above, the life-threatening arrhythmia discrimination method 1180 uses a single segment of data J 1004 (FIG. 10), rather than multiple segments discussed with respect to FIG. 11A. Blocks 1180-1192 of FIG. 11B generally follow the same procedures described with respect to blocks 1100-1150 in FIG. 11A. A number N of RR intervals 1008 that comprise a segment is selected 1182, and the duration of each RR interval 1108 is used to determine an instantaneous heart rate 1184 for each interval. The mean ("M") of the instantaneous heart rate values for the segment is calculated 1185. The mean is subtracted from the instantaneous heart rate values 1186, and the linear trend is removed 1188. The absolute deviation (the absolute value of the result from 1188) is calculated 1190 for each RR interval 1108 in the segment, and the absolute deviation median value ("V") is identified 1192.

At block 1193 a result is calculated that is used to determine if an electric shock or other intervention is indicated. It has been found that very good specificity and sensitivity for determining if intervention is appropriate can be achieved using a result comprising a linear combination of the instantaneous heart rate mean, M, and the median of the absolute deviation, V. In particular, a linear combination of M and V can be used to obtain a result that is then compared with a desired threshold, wherein if the result exceeds the threshold then intervention is indicated. This linear combination may be represented as: (A*M)+(B*V), where A and B are empirically obtained constant coefficient values.

In the current embodiment the empirically determined coefficients, A and B, have values in the ranges of 1.70 to 2.00 and −0.50 to −0.60 respectively. The coefficients A and B have preferred values of 1.875 and −0.53125, respectively. At block 1194 the result obtained at block 1193 is compared with a desired threshold. If the threshold is exceeded, the method proceeds to block 1196 where the method indicates that the type of arrhythmia detected requires electric shock. Otherwise, the method indicates that intervention is not indicated 1198.

Of course, it is possible to use data from the atrial fibrillation, normal sinus rhythm and ventricular tachyarrhythmia databases, such as the data from PhysioNet™ referenced above, to determine a suitable threshold for use in the present application, using the procedure outlined with reference to FIGS. 8 and 9.

Figure 12:
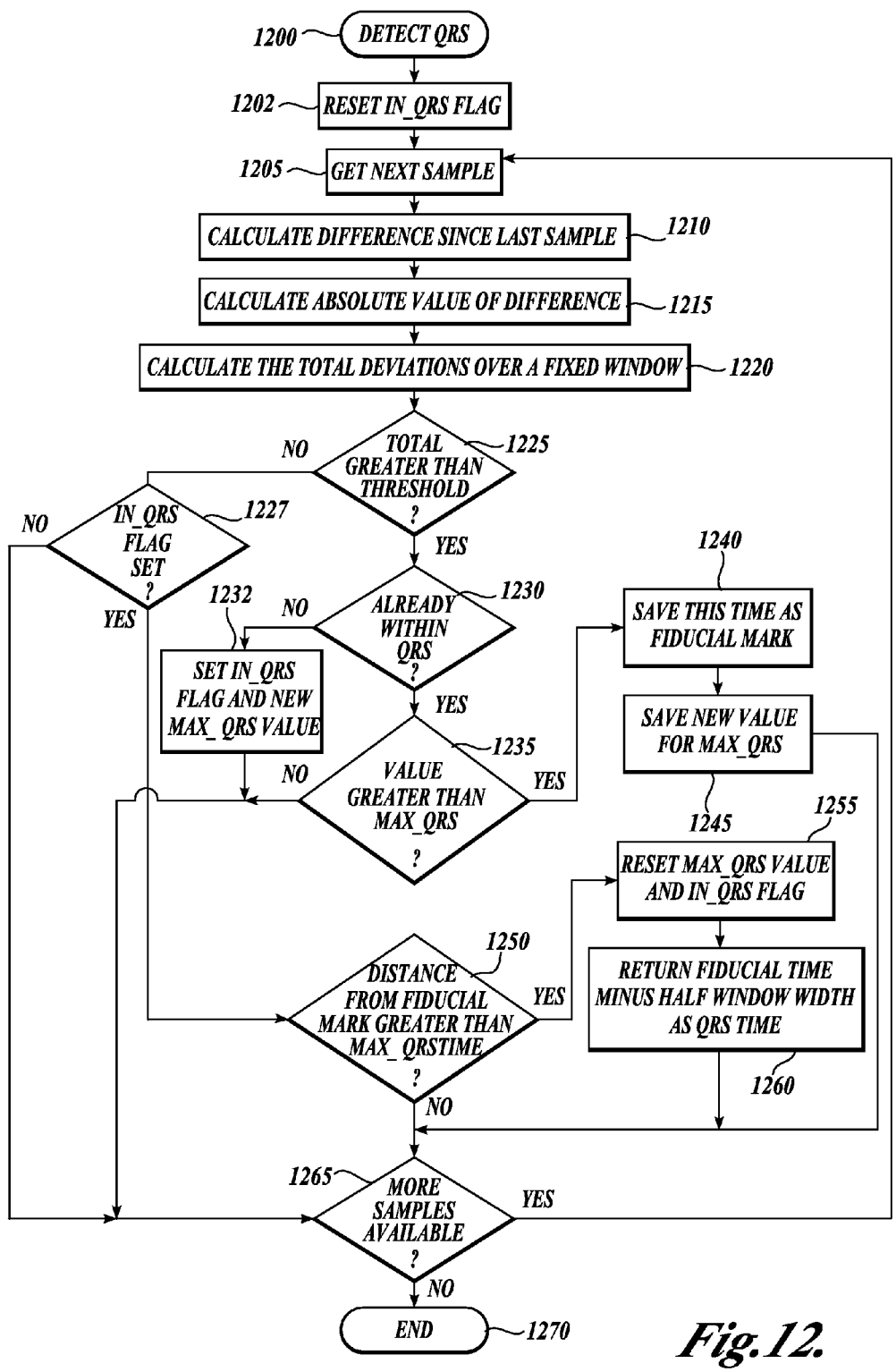
FIG. 12 is a flow diagram of an illustrative QRS detection method.

FIG. 12 is a flow diagram of an illustrative QRS detection method 1200. As discussed above with respect to FIG. 4B, method 1200 may be used by a software program executed by the microprocessor 458 to detect a QRS complex 602. The method 1200 detects the QRS complex 602 by summing up the absolute value of the amplitudes of the signal samples that fall within a QRS complex 602 time window and comparing the sum with a threshold. More specifically, in block 1202, an IN_QRS flag is reset. In block 1205, the next signal sample is obtained for detection of the QRS complex 602. In block 1210, an amplitude difference between the next signal sample and the immediate previous signal sample is calculated. In block 1215, an absolute value of the amplitude difference between the next and the immediate previous signal samples is calculated. In block 1220, the total of the absolute values of amplitude differences over a predetermined time window is calculated. In block 1225, the total of the absolute values of amplitude differences is compared with a threshold. If the total of the absolute values of amplitude differences is greater than the threshold, the flow diagram proceeds to block 1230 where it is determined whether the time of the next signal sample is within the time window of the QRS complex 602. Otherwise, the flow diagram proceeds to block 1250. Back in block 1230, if the time of the next signal sample is within the QRS complex 602, the flow diagram proceeds to block 1235 where it is determined whether the total of the absolute values of amplitude differences of the next signal sample is greater than a current maximum QRS amplitude value, MAX_QRS. If the total of the absolute values of amplitude differences is greater than MAX_QRS, the flow diagram proceeds to block 1240 where the time of the next signal sample is marked as a fiducial point. The flow diagram proceeds to block 1245 where the value of the maximum QRS is updated and set to the total of the absolute values of amplitude differences. The flow diagram proceeds to block 1265 where it is determined if more sample signals are available. If more sample signals are available, the flow diagram proceeds back to step 1205 to get the next signal sample. Otherwise, the flow diagram terminates at block 1270.

Back in block 1225, if the total of the absolute values of amplitude differences is not greater than the variation threshold, the flow diagram proceeds to block 1227 where the state of the IN_QRS flag is determined. If the IN_QRS flag is set, the flow diagram proceeds to block 1250. Otherwise, the flow diagram continues to block 1265. In block 1250, the flow determines whether the time distance from the fiducial mark is greater than a maximum QRS time value, MAX_QRSTIME. MAX_QRSTIME indicates the maximum time span that a QRS complex 602 may have. If the time distance from the fiducial mark is greater than the MAX_QRSTIME, the flow diagram proceeds to block 1255 where the MAX_QRS value and IN_QRS flag are reset. The flow diagram proceeds to block 1260, where the difference between the fiducial time and half the predetermined time window is provided by the method 1200 as the time of the QRS signal. Back in block 1230, if the time of the next signal is not within the QRS complex 602, the flow diagram proceeds to block 1232 where an IN_QRS flag is set to indicate the start of a new QRS complex 602, and a value is set for the maximum QRS. The flow diagram proceeds to block 1265 and continues as discussed above.

The methods and systems described above allow identification of patients at risk due to otherwise undetected atrial fibrillation. For example, studies may be performed to assess the risk as a function of the amount and duration of atrial fibrillation, in the patients known to have paroxysmal atrial fibrillation. These methods and systems could also allow automated or semi-automated treatment of atrial fibrillation, either with medications or electrical shocks (cardioversion).

The methods and systems also allow the prevention of inappropriate defibrillation (shocks) in individuals with an implantable cardiac defibrillator, while still allowing life-saving shocks.

While the preferred embodiment of the invention has been illustrated and described, it will be appreciated that various changes can be made therein without departing from the spirit and scope of the invention. For example, while the methods and systems described above are directed towards the detection of atrial fibrillation, and prevention of inappropriate shocks, other infrequent but clinically significant rhythm disturbances, such as ventricular tachycardia or intermittent high-grade atrioventricular block, may be detected by substantially similar methods and systems.

The embodiments of the invention in which an exclusive property or privilege is claimed are define as follows:

1. A wearable cardiac arrhythmia monitoring and detection device comprising:
   a substrate having a first end incorporating a first electrode, a second end incorporating a second electrode, and an intermediate portion connecting the first and second ends, the intermediate portion incorporating an integrated monitoring device;
   wherein the integrated monitoring device comprises: (i) an amplifier configured to receive and amplify electrocardiography data from the first and second electrodes; (ii) a programmable microprocessor configured to receive the electrocardiography data from the amplifier and to analyze the received data; (iii) a data storage device configured to receive and store at least a portion of the electrocardiography data from the programmable microprocessor; and (iv) a power supply; and further
   wherein the integrated monitoring device is configured to:
   (v) determine the duration of heart beat intervals from the electrocardiography data for a selected analysis segment comprising a plurality of heart beat intervals; (vi) calculate an instantaneous heart rate for each of the heart beat intervals in the analysis segment; (vii) calculate a test result using the calculated instantaneous heart rates; and (viii) compare the test result with a predetermined threshold to discriminate between different types of cardiac arrhythmia.

2. The wearable cardiac arrhythmia monitoring and detection device of claim 1, wherein the programmable microprocessor is configured to identify cardiac arrhythmia, and further wherein only electrocardiography data associated with detected cardiac arrhythmia is stored by the data storage device.

3. The wearable cardiac arrhythmia monitoring and detection device of claim 2, wherein the microprocessor compresses the electrocardiography data associated with detected atrial fibrillation prior to the data being stored by the data storage device.

4. The wearable cardiac arrhythmia monitoring and detection device of claim 2, wherein the cardiac arrhythmia comprises atrial fibrillation.

5. The wearable cardiac arrhythmia monitoring and detection device of claim 4, wherein the integrated monitoring device is configured to: (i) determine the duration of heart beat intervals from the electrocardiography data for a selected analysis segment comprising a plurality of heart beat intervals; (ii) calculate an instantaneous heart rate for each of the heart beat intervals in the analysis segment; (iii) calculate a test result using the calculated instantaneous heart rates; and (iv) compare the test result with a predetermined threshold to identify an event of atrial fibrillation.

6. The wearable cardiac arrhythmia monitoring and detection device of claim 4, wherein the integrated monitoring device is further configured to: (v) calculate a mean instantaneous heart rate for the analysis segment; (vi) calculate a deviation from the mean instantaneous heart rate for each heart beat interval in the analysis segment; and (vii) determine a median deviation from the mean instantaneous heart rate in the analysis segment; and wherein the test result is calculated using the mean instantaneous heart rate and the median deviation from the mean instantaneous heart rate.

7. The wearable cardiac arrhythmia monitoring and detection device of claim 6, wherein the test result is calculated as a linear combination of the mean instantaneous heart rate and the median deviation from the mean instantaneous heart rate.

8. The wearable cardiac arrhythmia monitoring and detection device of claim 1, wherein the analysis segment comprises between five and nineteen heart beat intervals.

9. The wearable cardiac arrhythmia monitoring and detection device of claim 1, wherein the integrated monitoring device further comprises a wave pattern detection device that is configured to receive electrocardiography data from the first and second electrodes.

10. The wearable cardiac arrhythmia monitoring and detection device of claim 9, wherein the wave pattern detection device is a QRS detector operable to detect a QRS complex signal from the received electrocardiography data, and to provide QRS information to the microprocessor.

11. The wearable cardiac arrhythmia monitoring and detection device of claim 9, wherein the wave pattern detection is performed by the microprocessor, and functions as a QRS detector operable to detect a QRS complex signal from the received electrocardiography data, and to provide QRS information to the microprocessor.

12. The wearable cardiac arrhythmia monitoring and detection device of claim 1, wherein the integrated monitoring device further comprises a wireless module configured to communicate data from the integrated monitoring device to an external computer.

13. A wearable atrial fibrillation monitoring and detection device comprising:
a substrate having a first end incorporating a first electrode, a second end incorporating a second electrode, and an intermediate portion with an embedded monitoring system;
wherein the embedded monitoring system comprises: (i) a preamplifier configured to receive electrocardiography data from the first and second electrodes; (ii) a microprocessor configured to receive the electrocardiography data from the amplifier and to analyze the received data; (iii) a data storage device configured to receive and store at least a portion of the electrocardiography data from the microprocessor; and (iv) a power supply; and further wherein the embedded monitoring system is configured to:
(v) determine the duration of heart beat intervals from the electrocardiography data for an analysis segment comprising a plurality of heart beat intervals; (vi) calculate an instantaneous heart rate for each of the heart beat intervals in the analysis segment; (vii) calculate a test result using the calculated instantaneous heart rates; and (viii) compare the test result with a predetermined threshold to identify an atrial fibrillation event.

14. The wearable atrial fibrillation monitoring and detection device of claim 13, wherein the microprocessor is configured to detect atrial fibrillation, and further wherein only electrocardiography data associated with detected atrial fibrillation is stored on the data storage device.

15. The wearable atrial fibrillation monitoring and detection device of claim 14, wherein the microprocessor compresses the electrocardiography data associated with detected atrial fibrillation prior to the data being stored on the data storage device.

16. The wearable atrial fibrillation monitoring and detection device of claim 14, wherein the embedded monitoring system is further configured to: (v) calculate a mean instantaneous heart rate for the analysis segment; (vi) calculate a deviation from the mean instantaneous heart rate for each heart beat interval in the analysis segment; and (vii) determine a median deviation from the mean instantaneous heart rate in the analysis segment; and wherein the test result is calculated using the mean instantaneous heart rate and the median deviation from the mean instantaneous heart rate.

17. The wearable atrial fibrillation monitoring and detection device of claim 16, wherein the test result is calculated as a linear combination of the mean instantaneous heart rate and the median deviation from the mean instantaneous heart rate.

18. The wearable atrial fibrillation monitoring and detection device of claim 14, wherein the analysis segment comprises between five and nineteen heart beat intervals.

19. The wearable atrial fibrillation monitoring and detection device of claim 13, wherein the embedded monitoring system further comprises a wave pattern detection device that is configured to receive electrocardiography data from the first and second electrodes.

20. The wearable atrial fibrillation monitoring and detection device of claim 19, wherein the wave pattern detection device is a QRS detector operable to detect a QRS complex signal from the received electrocardiography data, and to provide QRS information to the microprocessor.

21. The wearable atrial fibrillation monitoring and detection device of claim 19, wherein the wave pattern detection is performed by the microprocessor, and comprises a QRS detector operable to detect a QRS complex signal from the received electrocardiography data, and to provide QRS information to the microprocessor.

22. The wearable atrial fibrillation monitoring and detection device of claim 13, wherein the embedded monitoring system further comprises a wireless module configured to communicate data from the integrated monitoring device to an external computer.

\* \* \* \* \*